US011266460B2

(12) United States Patent
Hancock et al.

(10) Patent No.: US 11,266,460 B2
(45) Date of Patent: Mar. 8, 2022

(54) CABLE FOR CONVEYING RADIOFREQUENCY AND/OR MICROWAVE FREQUENCY ENERGY TO AN ELECTROSURGICAL INSTRUMENT

(71) Applicant: CREO MEDICAL LIMITED, Chepstow (GB)

(72) Inventors: Christopher Paul Hancock, North East Somerset (GB); Malcolm White, Chepstow (GB); George Christian Ullrich, Gwynedd (GB); David Edward Webb, Gwynedd (GB); Louis Turner, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 1290 days.

(21) Appl. No.: 15/517,864

(22) PCT Filed: Oct. 16, 2015

(86) PCT No.: PCT/EP2015/074036
§ 371 (c)(1),
(2) Date: Apr. 7, 2017

(87) PCT Pub. No.: WO2016/059222
PCT Pub. Date: Apr. 21, 2016

(65) Prior Publication Data
US 2017/0360497 A1 Dec. 21, 2017

(30) Foreign Application Priority Data
Oct. 17, 2014 (GB) ........................ 1418479

(51) Int. Cl.
*A61B 18/12* (2006.01)
*A61B 17/00* (2006.01)
*A61B 18/00* (2006.01)

(52) U.S. Cl.
CPC .... *A61B 18/12* (2013.01); *A61B 2017/00477* (2013.01); *A61B 2018/00065* (2013.01);
(Continued)

(58) Field of Classification Search
CPC .......... A61B 18/12; A61B 2017/00477; A61B 2018/00065; A61B 2018/126;
(Continued)

(56) References Cited

U.S. PATENT DOCUMENTS 3,532,095 A * 10/1970 Miller ................ A61B 18/1402
606/45
4,041,499 A * 8/1977 Liu ........................ H01Q 25/04
343/756

(Continued)

FOREIGN PATENT DOCUMENTS

GB 1172272 A 11/1969
JP 2010-540029 A 12/2010
(Continued)

OTHER PUBLICATIONS

Japanese Office Action from the Japanese Patent Office in counterpart application No. 2017-520953, dated Jul. 2, 2019.
(Continued)

*Primary Examiner* — William H. Mayo, III
*Assistant Examiner* — Krystal Robinson
(74) *Attorney, Agent, or Firm* — Arent Fox LLP

(57) ABSTRACT

Embodiments of the invention provide a hollow cable for transmitting radiofrequency and/or microwave frequency energy to an electrosurgical instrument, wherein the hollow cable is provided with electrical connectors for forming a bipolar electrical connection with an electrosurgical instrument that fits within, e.g. slides relative to, the hollow cable. The connectors can be conductive protrusions extending in an axial direction on opposite sides of the cable. The
(Continued)

protrusions can be tabs, fins, rods, pins, or wires. The protrusions can be strips which engage corresponding terminals on the instrument. The transmission line structure of the invention can have a greater diameter than conventional coaxial cables, which can minimize loss whilst still providing access for control wires and/or fluid to reach a surgical instrument. The cable can be used with multiple instruments.

30 Claims, 17 Drawing Sheets

(52) U.S. Cl.
CPC .............. *A61B 2018/00148* (2013.01); *A61B 2018/126* (2013.01); *H01R 2201/12* (2013.01)

(58) Field of Classification Search
CPC ...... A61B 2018/00148; A61B 18/1815; A61B 18/22; A61B 1/00114; A61B 17/29; A61B 17/32002; A61B 17/3207; A61B 18/245; H01R 2201/12; H01R 103/00; H01R 13/113; H01R 13/5216; H01R 13/6583; H01R 43/16; H01R 4/184; H01R 4/20; H01R 9/0518; H01R 4/70; H01R 13/2435; H01R 13/405; H01R 13/5808; H01R 13/6585; H01R 13/6589; H01R 24/40; H01R 33/02; H01R 43/24; H01R 4/185; H01R 9/0521; H01R 12/774; H01R 12/79; H01R 13/41; H01R 13/504; H01R 13/5045; H01R 13/533; H01R 24/30; H01R 4/18; H01R 4/56; H02G 15/046; H02G 15/007; H02G 15/013; H02G 15/06; H02G 15/068; H02G 3/0666; H02G 5/10; H01B 9/04
See application file for complete search history.

(56) References Cited

U.S. PATENT DOCUMENTS

| | | | | |
|---|---|---|---|---|
| 4,545,375 A | * | 10/1985 | Cline | A61B 18/1402 200/302.2 |
| 4,655,215 A | * | 4/1987 | Pike | A61B 18/1402 606/42 |
| 4,674,499 A | | 6/1987 | Pao | |
| 5,573,424 A | * | 11/1996 | Poppe | A61B 18/14 439/502 |
| 5,574,815 A | | 11/1996 | Kneeland | |
| 5,989,249 A | * | 11/1999 | Kirwan, Jr. | A61B 18/14 606/40 |
| 6,878,147 B2 | * | 4/2005 | Prakash | A61B 18/18 606/33 |
| 9,119,650 B2 | * | 9/2015 | Brannan | A61B 34/25 |
| 2001/0002811 A1 | * | 6/2001 | Gregorwich | H01P 1/30 333/245 |
| 2001/0016750 A1 | * | 8/2001 | Malecki | A61B 17/34 606/158 |
| 2001/0034159 A1 | * | 10/2001 | Pitschi | H01R 9/05 439/583 |
| 2001/0047132 A1 | * | 11/2001 | Johnson | G01R 33/341 600/410 |
| 2003/0088242 A1 | * | 5/2003 | Prakash | A61B 18/1815 606/33 |
| 2003/0109862 A1 | | 6/2003 | Prakash et al. | |
| 2004/0049254 A1 | * | 3/2004 | Longo | A61B 18/1815 607/116 |
| 2004/0220557 A1 | * | 11/2004 | Eum | A61B 18/04 606/21 |
| 2008/0033424 A1 | * | 2/2008 | van der Weide | A61B 18/1815 606/41 |
| 2009/0187180 A1 | | 7/2009 | Brannan | |
| 2009/0275940 A1 | | 11/2009 | Malackowski et al. | |
| 2009/0299360 A1 | | 12/2009 | Ormsby | |
| 2010/0178799 A1 | * | 7/2010 | Lee | H01R 9/0527 439/578 |
| 2011/0118723 A1 | * | 5/2011 | Turner | A61B 18/1815 606/33 |
| 2012/0172860 A1 | * | 7/2012 | Brannan | A61B 18/1815 606/33 |
| 2013/0289557 A1 | * | 10/2013 | Hancock | A61B 18/1815 606/33 |
| 2019/0199014 A1 | * | 6/2019 | Kanemura | H01R 13/6583 |

FOREIGN PATENT DOCUMENTS

| | | |
|---|---|---|
| WO | WO 2008/028980 A2 | 3/2008 |
| WO | WO 2008/069462 A1 | 6/2008 |
| WO | WO 2009/039093 A2 | 3/2009 |
| WO | WO 2009/120119 A1 | 10/2009 |
| WO | WO 2011/066445 A2 | 6/2011 |

OTHER PUBLICATIONS

British Search and Examination Report of related British Patent Application No. 1518347.8 dated Jan. 13, 2016.
British Search Report of related British Patent Application No. 1418479.0 dated Apr. 15, 2015.
International Preliminary Report on Patentability of related International Patent Application No. PCT/EP2015/074036 dated Feb. 2, 2017.
International Search Report of related International Patent Application No. PCT/EP2015/074036 dated Dec. 15, 2015.
Written Opinion of related International Patent Application No. PCT/EP2015/074036 dated Oct. 6, 2016.

* cited by examiner

CABLE FOR CONVEYING RADIOFREQUENCY AND/OR MICROWAVE FREQUENCY ENERGY TO AN ELECTROSURGICAL INSTRUMENT

CROSS-REFERENCE TO RELATED APPLICATIONS

This application is a National Stage Entry of International Patent Application No. PCT/EP2015/074036, filed Oct. 16, 2015, which claims priority to British Patent Application No. 1418479.0, filed Oct. 17, 2014. The disclosures of the priority applications are incorporated in their entirety herein by reference.

FIELD OF THE INVENTION

The present invention relates to a cable for conveying radiofrequency and/or microwave frequency energy to an electrosurgical instrument, and in particular to such a cable comprising a hollow tube.

BACKGROUND TO THE INVENTION

Electrosurgical instruments are instruments that are used to deliver radiofrequency and/or microwave frequency energy to biological tissue, for purposes such as cutting biological tissue or coagulating blood. Radiofrequency and/or microwave frequency energy is supplied to the electrosurgical instrument using a cable. Conventional cables used for this purpose have a coaxial transmission line structure comprising a solid cylindrical inner conductor, a tubular layer of dielectric material around the inner conductor, and a tubular outer conductor around the dielectric material.

When operating many electrosurgical instruments it is common to need to provide additional supplies or components (e.g. control means) to the electrosurgical instrument, such as a liquid or gas feed, liquids or gasses, or guide- or pull-wires for manipulating (for example opening/closing, rotating or extending/retracting) part(s) of the electrosurgical instrument.

In order to provide these additional supplies or components to the electrosurgical instrument, additional structures have been provided together with the conventional cable, such as additional tubes adjacent to the conventional cable. For example, it is known to provide an additional tube housing a pull-wire for the electrosurgical instrument alongside the conventional cable, and to house the conventional cable and the tube housing the pull-wire within a single protective jacket/casing.

SUMMARY OF THE INVENTION

The present inventors have realised that conventional cables for conveying radiofrequency and/or microwave energy to an electrosurgical instrument, which have the coaxial transmission line structure described above, suffer from various disadvantages.

In particular, the present inventors have realised that with a conventional arrangement for providing everything needed by the electrosurgical instrument in use, which includes a conventional cable and other structures such as an additional tube for housing a pull-wire, significant amounts of space are wasted, and for a given overall size (diameter) of the arrangement the maximum possible size (diameter) of the cable is limited, which may lead to significant power losses occurring in the cable.

Furthermore, the present inventors have realised that with the conventional arrangement, additional components such as pull-wires are positioned towards the edges of the arrangement, and this off-centre configuration may cause problems when operating the electrosurgical instrument using the additional components.

The present inventors have realised that one or more of these problems may be addressed by providing a cable that is hollow, so that one or more additional components can be passed through the cable in use. By positioning one or more of the additional components inside the cable, the size (diameter) of the cable can be maximised, which may reduce power losses occurring in the cable, because less space around the cable is required for additional structures. Furthermore, by positioning an additional component such as a pull-wire inside the cable, it may be possible to deliver actuation to the electrosurgical instrument down (or closer to) the centre of the cable, which may improve the actuation of the electrosurgical instrument.

The present inventors have also realised that such a hollow cable is achievable in practice because of the skin-depth effect when transmitting microwave frequency energy, which means that microwave frequency energy travels only in a shallow surface area of a conductor. The present inventors have also realised that radiofrequency energy can be suitably conveyed along such a hollow cable, despite the use of thin conductors in such a cable increasing the resistance, loss and heating in the cable compared to the use of thicker conductors.

At its most general, the present invention relates to a hollow cable for transmitting radiofrequency and/or microwave frequency energy to an electrosurgical instrument, wherein the hollow cable is provided with electrical connectors for forming a bipolar electrical connection with the electrosurgical instrument.

According to an aspect of the present invention there is provided a cable for conveying radiofrequency and/or microwave frequency energy to an electrosurgical instrument at a first end of the cable, the cable comprising:

a hollow tube comprising inner and outer electrically conductive layers separated by dielectric material to form a transmission line;

a first terminal at the first end of the cable, the first terminal being arranged to form an electrical connection between the inner conductive layer and a first cooperating terminal of the electrosurgical instrument;

a second terminal at the first end of the cable, the second terminal being arranged to form an electrical connection between the outer conductive layer and a second cooperating terminal of the electrosurgical instrument.

Thus, the cable can be connected to an electrosurgical instrument to form a bipolar electrical connection with the electrosurgical instrument by electrically connecting the first terminal and the first cooperating terminal and by electrically connecting the second terminal and the second cooperating terminal. The cable can then be used to convey radiofrequency or microwave frequency energy to the electrosurgical instrument.

In some embodiments, the cable may be for conveying only radiofrequency energy to the electrosurgical instrument. In other embodiments, the cable may be for conveying only microwave frequency energy to the electrosurgical instrument. In further embodiments, the cable may be for conveying both radiofrequency energy and microwave frequency energy to the electrosurgical instrument.

The term inner means closer to a centre of the hollow tube. The term outer means further from a centre of the hollow tube.

The tube may be a cylindrical tube in which the inner conductive layer and the outer conductive layer are concentric (coaxial) layers. In this case, the term inner means radially inner, and the term outer means radially outer.

The term hollow means that the tube has a bore or lumen extending along its length, for example centred on a centre of the tube.

The term conductive is used in the present invention to mean electrically conductive, unless the context dictates otherwise.

An electrosurgical instrument may be any instrument, or tool, which is used during surgery and which utilises radiofrequency or microwave frequency energy. Herein, radiofrequency (RF) may mean a stable fixed frequency in the range 10 kHz to 300 MHz and microwave energy may mean electromagnetic energy having a stable fixed frequency in the range 300 MHz to 100 GHz. The RF energy should have a frequency high enough to prevent the energy from causing nerve stimulation and low enough to prevent the energy from causing tissue blanching or unnecessary thermal margin or damage to the tissue structure. Preferred spot frequencies for the RF energy include any one or more of: 100 kHz, 250 kHz, 400 kHz, 500 kHz, 1 MHz, 5 MHz. Preferred spot frequencies for the microwave energy include 915 MHz, 2.45 GHz, 5.8 GHz, 14.5 GHz, 24 GHz.

The hollow nature of the cable means other components needed in use of the electrosurgical instrument, such as a gas or liquid feed, or a pull-wire or other control means, can be fed up through the inside of the cable. This means the outer diameter of the cable can be maximised relative to an arrangement in which the other components have to be positioned around the outside of the cable. Maximising the diameter of the cable reduces power losses in the cable relative to a smaller diameter cable. The cable may therefore be able to deliver more power to the electrosurgical instrument relative to a conventional cable. Furthermore, actuating components such as pull-wires may be positioned close to a centre of the cable, which may improve actuation of the electrosurgical instrument.

Additional components, such as actuating controls or gas or liquid feeds, that are passed through the hollow tube of the cable may be arranged in a concentric arrangement in the hollow tube of the cable. This may optimise the use of space in the hollow tube of the cable.

The first and second terminals may be arranged to form the electrical connections to the first and second corresponding terminals of the electrosurgical instrument by being electrically connected to the inner conductive layer or the outer conductive layer respectively and by being positioned where they are accessible to the corresponding terminals of the electrosurgical instrument.

The transmission line may be a coaxial transmission line in which the inner and outer conductive layers are coaxial.

The first end of the cable is the end of the cable that is for connecting (either directly or indirectly through another component or part) to the electrosurgical instrument. In other words, the first end of the cable is the distal end of the cable.

The opposite, second end of the cable is for connecting the cable to a generator for supplying radiofrequency and/or microwave frequency energy to the cable. In other words, the second end of the cable is the proximal end of the cable. The second end of the cable may have a terminal or connector for connecting the second end of the cable to a generator. Thus, the cable may be for conveying radiofrequency and/or microwave frequency energy from a generator connected to the second (proximal) end of the cable to an electrosurgical instrument connected to the first (distal) end of the cable.

The first terminal may comprise an end of the inner conductive layer, for example an end of the inner conductive layer exposed on a face of the cable at the first end of the cable, or a circumferential surface of the inner conductive layer at the end of the inner conductive layer.

The second terminal may comprise an end of the outer conductive layer, for example an end of the outer conductive layer exposed on a face of the cable at the first end of the cable, or a circumferential surface of the outer conductive layer at the end of the outer conductive layer.

An electrical connection between a terminal and a corresponding terminal at its most general means an interface between the terminal and the corresponding terminal where an electrical signal can be passed from the terminal to the corresponding terminal. For example, there may be direct contact between the terminal and the corresponding terminal so that current flows directly between them, or an indirect galvanic connection through an intermediate conductive material or medium, for example a conductive adhesive or bonding material. Alternatively, an electrical signal may be passed from the terminal to the corresponding terminal through some other type of electrical coupling, for example inductive or capacitive coupling, or other types of magnetic and/or electrical coupling, for example a transformer.

The cable according to the aspect of the present invention may have any one or, to the extent that they are compatible, any combination of the following optional features.

The first terminal may comprise a first electrically conductive protrusion extending in an axial direction from the first end of the cable and electrically connected to the inner conductive layer. The first conductive protrusion may be any conductive part that projects, sticks out, or extends from the first end of the cable in a generally axial direction. The first conductive protrusion may not extend solely in the axial direction (i.e. parallel to the axial direction) and instead may also extend in an outward (for example radial) direction of the cable. In other words, the first conductive protrusion may extend at an angle to the axial direction. The first conductive protrusion may be formed integrally with a part of the cable, or attached or connected to the cable.

The first conductive protrusion may be arranged (for example located and/or shaped) to be received in a corresponding first recess of the electrosurgical instrument, for example formed on an end face of the electrosurgical instrument. In other words, the first corresponding terminal of the electrosurgical instrument may be a corresponding first recess on the electrosurgical instrument for receiving the first conductive protrusion. An electrical connection between the inner conductive layer and the electrosurgical instrument may therefore be formed by the first conductive protrusion being received in the corresponding first recess.

The second terminal may comprise a second electrically conductive protrusion extending in an axial direction from the first end of the cable and electrically connected to the outer conductive layer. The second conductive protrusion may be any conductive part that projects, sticks out, or extends from the first end of the cable in a generally axial direction. The second conductive protrusion may not extend solely in the axial direction (i.e. parallel to the axial direction) and instead may also extend in an outward (for example radial) direction of the cable. In other words, the second conductive protrusion may extend at an angle to the axial direction. The second conductive protrusion may be formed integrally with a part of the cable, or attached or connected to the cable.

The second conductive protrusion may be arranged (for example located and/or shaped) to be received in a corresponding second recess of the electrosurgical instrument, for example formed on an end face of the electrosurgical instrument. In other words, the second corresponding terminal of the electrosurgical instrument may be a corresponding second recess on the electrosurgical instrument for receiving the second conductive protrusion. An electrical connection between the outer conductive layer and the electrosurgical instrument may therefore be formed by the second conductive protrusion being received in the corresponding second recess.

The first conductive protrusion and/or the second conductive protrusion may be rigid. Therefore, the first conductive protrusion and/or the second conductive protrusion may provide a secure mechanical connection between the cable and the electrosurgical instrument in addition to providing the above described electrical connection. For example, where the first conductive protrusion and second conductive protrusion are received in corresponding recesses on a face of the electrosurgical instrument, the cable may be electrically and mechanically connected to the electrosurgical instrument by the conductive protrusions being received in the corresponding recesses.

The first conductive protrusion and/or the second conductive protrusion may comprise a conductive tab, a conductive fin, a conductive rod, a conductive pin, a conductive wire, or indeed any other elongate conductive member.

The first conductive protrusion and/or the second conductive protrusion may be made of metal.

The first terminal and the second terminal may be located on opposite sides of the cable relative to a central axis of the cable. In other words, the first terminal and the second terminal may both lie on a line perpendicular to the central axis of the cable and passing through the central axis of the cable. This configuration may facilitate connection of the cable to the electrosurgical instrument and, where the first terminal and the second terminal comprise rigid protrusions, may also improve the strength and stability of the mechanical connection between the cable and the electrosurgical instrument.

The first conductive protrusion may extend in the axial direction from an electrically conductive strip positioned around the inner conductive layer and electrically connected to the inner conductive layer, wherein the first conductive protrusion may be integral with the electrically conductive strip. For example, the electrically conductive strip may substantially surround the inner conductive layer and the first conductive protrusion may extend from part of an edge of the electrically conductive strip.

The electrically conductive strip may be covered by a tubular section, for example a small section of dielectric tube, and an edge of the tubular section may be flush with an edge of the inner conductive layer with the first conductive protrusion extending beyond the edge of the tubular section.

The second conductive protrusion may extend in the axial direction from an electrically conductive strip positioned around the outer conductive layer and electrically connected to the outer conductive layer, wherein the second conductive protrusion is integral with the electrically conductive strip. For example, the electrically conductive strip may substantially surround the outer conductive layer and the second conductive protrusion may extend from part of an edge of the electrically conductive strip.

The first conductive protrusion, and/or the second conductive protrusion, and the integral conductive strip may comprise conductive foil, for example a conductive metal foil.

Where the cable comprises the first conductive protrusion and the second conductive protrusion, the first conductive protrusion and the second conductive protrusion may be supported by a tube segment connected to the first end of the cable. For example, an end of the cable may have an angled surface and a tube segment having a corresponding angled surface may be connected to the end of the cable. The tube segment may support the first conductive protrusion and the second conductive protrusion by having corresponding channels, bores or lumens for receiving the first conductive protrusion and the second conductive protrusion. The tube section may be shaped so that the first conductive protrusion and the second conductive protrusion extend from a second end of the tube section when a first end of the tube section is attached to the cable. The first conductive protrusion and the second conductive protrusion may be attached or secured to the tube section. The term tube section means a short length of tube.

The first conductive protrusion may be electrically connected to the inner conductive layer in a region where the dielectric material and outer conductive layer are omitted. For example, a part or section of the outer conductive layer and the dielectric material may be cut away or removed to expose a region of the inner conductive layer on an outer circumferential surface of the cable. The first conductive protrusion can then be electrically connected to the inner conductive layer by being brought into physical (or electrical) contact with the exposed region of the inner conductive layer. This may enable the first conductive protrusion to be connected to the inner conductive layer without the first conductive protrusion extending significantly into the hollow inside of the cable or the outside of the cable. The remainder of the exposed region may then be covered with an insulating material, such as an insulating adhesive.

The second conductive protrusion may be electrically connected to the outer conductive layer in a region where the dielectric material and inner conductive layer are omitted. For example, a part or section of the inner conductive layer and the dielectric material may be cut away or removed to expose a region of the outer conductive layer on an inner circumferential surface of the cable. The second conductive protrusion can then be electrically connected to the outer conductive layer by being brought into physical (or electrical) contact with the exposed region of the outer conductive layer. This may enable the second conductive protrusion to be connected to the outer conductive layer without the second conductive protrusion extending significantly into the hollow inside of the cable or the outside of the cable. The remainder of the exposed region may then be covered with an insulating material, such as an adhesive.

Alternatively, the first terminal may comprise a first area of electrically conductive material located on a circumferential surface of the cable. The first area of electrically conductive material may be a metal coated region of a surface of the cable. The surface may be an inner or an outer circumferential surface of the cable.

The first area of electrically conductive material may be exposed at an end face of the cable. For example, the first area of electrically conductive material may extend to an end face of the cable, so that an edge of the first area of electrically conductive material is exposed (i.e. visible or accessible) at the end face of the cable. Alternatively, the first area of electrically conductive material may comprise a further portion formed on an end face of the cable and electrically coupled to the remainder of the first area of electrically conductive material. With this arrangement, an electrical connection to the first area of electrically conductive material may be made by bringing a terminal of the electrosurgical instrument on a face of the electrosurgical instrument into contact with the exposed part of the first area of electrically conductive material.

The second terminal may comprise a second area of electrically conductive material located on a circumferential surface of the cable. The second area of electrically conductive material may be a metal coated region of a surface of the cable. The surface may be an inner or an outer circumferential surface of the cable. The second area of electrically conductive material may be formed on the same circumferential surface of the cable as the first area of electrically conductive material, which may facilitate connecting the cable to the electrosurgical instrument.

The second area of electrically conductive material may be exposed at an end face of the cable. For example, the second area of electrically conductive material may extend to an end face of the cable, so that an edge of the second area of electrically conductive material is exposed (i.e. visible or accessible) at the end face of the cable. Alternatively, the second area of electrically conductive material may comprise a further portion formed on an end face of the cable and electrically coupled to the remainder of the second area of electrically conductive material. With this arrangement, an electrical connection to the second area of electrically conductive material may be made by bringing a terminal of the electrosurgical instrument on a face of the electrosurgical instrument into contact with the exposed part of the second area of electrically conductive material.

The first area of electrically conductive material may be located on an outer side of the dielectric material and may be electrically connected to the inner conductive layer by an electrical connection that passes through, or around, the dielectric material. Being located on an outer side of the dielectric material may mean that the first area of electrically conductive material is formed on an outer surface of the dielectric material, or on an outer surface of another layer formed on the outer surface of the dielectric material. Thus, in this arrangement an electrical connection to the inner conductive layer can be made with a terminal located outside of the dielectric layer, which may facilitate connecting the cable to the electrosurgical instrument.

The first area of electrically conductive material may comprise a portion of the outer electrically conductive layer that is electrically isolated from the remainder of the outer electrically conductive layer. For example, the first area of electrically conductive material may be formed by selectively removing parts of the outer electrically conductive layer, for example by etching. Alternatively, the first area of electrically conductive material may be selectively formed in a region separated from the remainder of the outer electrically conductive layer.

The electrical connection may comprise a conductive material positioned in a hole through the dielectric material. In other words, a hole may be formed in the dielectric material between the first area of electrically conductive material and the inner conductive layer, and this hole may be filled with a conductive material. Thus, an electrical connection can be provided between the first area of electrically conductive material and the inner conductive layer. Alternatively, the electrical connection may comprise a conductive path, for example conductive material, positioned around an edge of the dielectric material, for example at the face of the cable at the first end of the cable.

The second terminal may comprise a conductive area located on an outer side of the dielectric material that is part of, or electrically connected to, the outer conductive layer. Thus, both the first and second terminal may be provided on a same outer circumferential surface of the cable, which may facilitate connecting the cable to the electrosurgical instrument.

The first conductive area and the second conductive area may be at different locations on a circumferential surface of the cable and electrically isolated from each other. For example, they may be positioned on opposite sides of the cable. The first conductive area and the second conductive area may be at the same axial position on the cable.

Alternatively, the second area of electrically conductive material may be located on an inner side of the dielectric material and may be electrically connected to the outer conductive layer by an electrical connection that passes through, or around, the dielectric material. Being located on an inner side of the dielectric material may mean that the second area of electrically conductive material is formed on an inner surface of the dielectric material, or on an inner surface of another layer formed on the inner surface of the dielectric material. Thus, in this arrangement an electrical connection to the outer conductive layer can be made with a terminal located inside of the dielectric layer, which may facilitate making such an electrical connection.

The second area of electrically conductive material may comprise a portion of the inner electrically conductive layer that is electrically isolated from the remainder of the inner electrically conductive layer. For example, the second area of electrically conductive material may be formed by selectively removing parts of the inner electrically conductive layer, for example by etching. Alternatively, the first area of electrically conductive material may be selectively formed in a region separated from the remainder of the inner electrically conductive layer.

The electrical connection may comprise a conductive material positioned in a hole through the dielectric layer. In other words, a hole may be formed in the dielectric material between the second area of electrically conductive material and the outer conductive layer, and this hole may be filled with a conductive material. Thus, an electrical connection can be provided between the second area of electrically conductive material and the outer conductive layer. Alternatively, the electrical connection may comprise a conductive path, for example conductive material, positioned around an edge of the dielectric material, for example at the face of the cable at the first end of the cable.

The first terminal may comprise a conductive region located on an inner side of the dielectric material that is part of, or electrically connected to, the inner conductive layer. Thus, both the first and second terminal may be provided on a same inner circumferential surface of the cable, which may facilitate connecting the cable to the electrosurgical instrument.

The first conductive area and the second conductive area may be at different locations on a circumferential surface of the cable and electrically isolated from each other. For example, they may be positioned on opposite sides of the cable. The first conductive area and the second conductive area may be at the same axial position on the cable.

The cable may comprise one or more protrusions or recesses for cooperating with corresponding protrusions or recesses on an end of the electrosurgical instrument for aligning the electrosurgical instrument with respect to the cable. This may aid orientation (i.e. rotational or angular alignment) of the electrosurgical instrument with the cable, for example so that the corresponding terminals of the electrosurgical instrument are appropriately aligned with the first and second terminals of the cable.

The inner conductive layer may be provided on an outer surface of a tube of material, and an edge of the tube of material may be set back with respect to an edge of the dielectric material. In other words, the edges of the dielectric material and the tube of material may be staggered, with the edge of the dielectric material protruding (sticking out) beyond the edge of the tube of material. This staggered arrangement may provide a good surface for connecting a tool to the cable, for example without having to go larger than the outer diameter of the cable or smaller than an inside diameter of the hollow cable.

The geometries (for example the size, shape, position, angular spread around the central axis) of the first terminal and the second terminal may be configured to substantially match the impedance of the cable to a predetermined impedance (for example a known impedance of an electrosurgical instrument) at one or more microwave frequencies. In other words, the geometry (e.g. sizes and/or shapes) of the first and second terminals may be selected or predetermined, based in part on knowledge of the configuration of the electrosurgical instrument, so that the impedance of the cable is substantially matched to the impedance of the electrosurgical instrument at the connection. This will substantially prevent reflection of power at the connection due to impedance mismatch, and thus increase the amount of power delivered to the electrosurgical instrument.

For example, where the terminals comprise the first and second areas of electrically conductive regions discussed above, the lengths and/or widths of the first and second areas may be selected, for example based on the results of simulations and/or tests and/or measurements, to match the impedance of the cable to the impedance of the electrosurgical tool at the microwave frequency of interest.

The cable may be configured to convey radiofrequency energy to the electrosurgical instrument with the transmission line and a further conductor positioned in the hollow tube and extending along the hollow tube, and the further conductor may be electrically insulated from the transmission line within the hollow tube of the cable. A possible problem with transmitting both radiofrequency energy and microwave frequency energy down the same transmission line of the cable is that the high voltage radiofrequency energy may cause breakdown of the dielectric material, particularly in porous, low loss materials that are particularly suitable for use in conveying microwave frequencies. Therefore, in some embodiments the radiofrequency signal may instead be conveyed using the transmission line and a further conductor positioned in the hollow tube and extending along the hollow tube. This may significantly reduce the risk of breakdown of the dielectric material.

The cable may be configured to convey radiofrequency energy in this way by having a terminal or connector at its second (proximal) end for connecting to a generator for supplying radiofrequency energy to the further conductor and the transmission line.

Electrically insulating the further conductor from the transmission line within the hollow cable may prevent electrical breakdown of air between the further conductor and the transmission line, which would otherwise damage the cable or increase the power loss in the cable. This may be achieved with an insulating layer around the further conductor (e.g. provided on a surface of the further conductor) or an insulating layer provided on an innermost surface of the cable, for example.

The cable may be configured to convey radiofrequency energy to the electrosurgical instrument with (only) the inner conductive layer and the further conductor, or with (only) the outer conductive layer and the further conductor, or with the inner conductive layer, the outer conductive layer, and the further conductor, wherein the inner conductive layer and the outer conductive layer are electrically connected at the second (proximal) end of the cable.

The conductor positioned in the hollow tube may be a conductive rod or tube used specifically for this purpose. Alternatively, the further conductor may comprise a further tubular conductive layer of the cable, for example an innermost tubular layer of the cable. Alternatively, an additional component being passed through the hollow tube may function as the central conductor. For example, a tube used to supply liquid or gas to the electrosurgical instrument, or a housing for a guide- or pull-wire may be formed of, or coated with, a conducting material and may act as the central conductor. A generator may then be used to input the radiofrequency signal into the cable using the transmission line and the further conductor separately from the microwave frequency signal, which is input to the inner and outer conductive layers of the transmission line only.

With an arrangement such as this it may be necessary to provide a configuration, such as a diplexer, at the first end of the cable to prevent the higher voltage radiofrequency signal from travelling back along the inner and outer conductors, and/or to prevent the microwave signal from travelling back along the further conductor. Alternatively, the further conductor may be configured so that it can be physically disconnected when using the cable to only convey microwave energy. For example, this may be achieved by pulling the further conductor axially away from the electrosurgical instrument so that it is no longer in contact with a corresponding terminal of the electrosurgical instrument.

The cable may comprise a conductor positioned in the hollow tube and extending along the hollow tube for conveying radiofrequency energy to the electrosurgical instrument with the transmission line.

The dielectric material may comprise a solid tube of dielectric material; or a tube of dielectric material having a porous structure. Being a solid tube of dielectric material may mean that the dielectric material is substantially homogeneous. Having a porous structure may means that the dielectric material is substantially inhomogeneous, with a significant number or amount of air pockets or voids.

For example, a porous structure may mean a honeycomb structure, a mesh structure, or a foam structure.

The dielectric material may comprise PTFE, or another low-loss microwave dielectric.

The dielectric material may comprise a tube with a thickness of greater than 0.2 mm, for example a tube with a thickness of 0.3 mm or 0.4 mm. In one embodiment, the dielectric material may be a tube of PTFE having an inner diameter of 1.6 mm and an outer diameter of 2.4 mm, for example.

The inner conductive layer and/or the outer conductive layer may comprise: a conductive coating on the inside or outside of a tube of material; a solid tube of conductive material positioned against the inside or outside of a tube of material; or a layer of braided conductive material formed on, or embedded in, a tube of material.

The conductive coating or the conductive material may be a metal, such as silver, gold or copper. Alternatively, the conductive coating or the conductive material may comprise a different type of conductive material, such as graphene. The conductive coating and the conductive material are preferably good conductors, i.e. low loss conductors at microwave frequencies or radiofrequencies, for example not steel.

The inner and/or the outer conductive layer may comprise a silver coating.

The inner and/or the outer conductive layer may have a thickness of approximately 0.01 mm.

Instead of being projections, in one embodiment the first and/or second terminal may comprise a recess, for example formed in an end face of the cable, for receiving a corresponding conductive protrusion of the electrosurgical instrument, for example formed on an end face of the electrosurgical instrument. Thus, an electrical, and possibly also a mechanical, connection is made between the cable and the electrosurgical instrument by positioning the electrosurgical instrument so that first and second conductive protrusions of the electrosurgical instrument are received in, and electrically connected to, corresponding first and second recesses of the cable.

Where the cable is for conveying only radiofrequency energy to the electrosurgical instrument and not microwave frequency energy, it is not necessary for the dielectric material to be a good microwave dielectric. Instead, in these embodiments the dielectric material may be a good radiofrequency dielectric material, for example a material that provides a stand-off or break down voltage that is sufficiently greater than the voltage of the radiofrequency signal, i.e. a material that has a sufficiently high dielectric strength. The dielectric material may also be selected at least in part based on its mechanical properties, such as its hardness, strength, or ease of plating. A suitable material may be Kapton, for example Kapton Polyimide film which has a breakdown strength of around 3000 KV/mm. Thus, in the following PTFE may be replaced with Kapton or Kapton Polyimide or another suitable radiofrequency dielectric when the cable is to be used for conveying only radiofrequency energy to the electrosurgical instrument.

Where only radiofrequency energy is being conveyed, reflection of energy due to impedance mismatch at the region where the cable is connected to the electrosurgical instrument is less significant that when conveying microwave frequency energy. Thus, it may be simpler to connect the cable to the electrosurgical instrument, and this could be achieved for example with two appropriate connected wires (in addition to the connection arrangements discussed below).

In some embodiments, a single conductor monopolar tool may be introduced into the cable and connected to the inner conductive layer only.

A protective covering or liner may be provided on an inner side of the inner metal layer to protect the inner metal layer, for example from damage caused by components or tools being passed through the hollow cable. In one embodiment, the protective liner may comprise an inner tubular layer, and the inner metal layer may be coated on an outer surface of the inner tubular layer. The inner tubular layer may comprise an insulating material, or a dielectric material.

In some embodiments, there may be a plurality or first terminals and/or a plurality of second terminals. For example, the plurality of first terminals and/or the plurality of second terminals may be symmetrically distributed around the central axis of the cable. The first and second terminals may be alternately positioned around the central axis of the cable.

In one embodiment, the first end of the cable may be detachable or otherwise separable from the remainder of the cable, for example so that different first ends having different configurations of the first and second terminals may be used with the same cable by attaching them to the cable. In another embodiment, the first end of the cable may be integral or fixed to the cable.

A protective outer sheath or outer coating (for example a spray coating) may be present on an outer surface of the cable, to protect the outer surface of the cable. This may comprise an insulating material for example, and/or a material chosen for its mechanical properties, such as strength and/or hardness.

In one configuration the cable may comprise a hollow inner tubular layer; a tube of the inner conductive layer on an outer surface of the hollow inner tubular layer; a tube of the dielectric material on an outer surface of the tube of the inner conductive layer; and a tube of the outer conductive layer on an outer surface of the tube of the dielectric material. The structure may, or may not, comprise air gaps between some or all of these layers. An advantage of avoiding air gaps is that losses in the cable may be minimised. In one example, this structure could be manufactured by sequentially coating each subsequent layer over the preceding (inner) layer. Alternatively, this structure could be made by forming one or more of the layers as a first part and one or more of the layers as a second part, and then sliding one part inside of the other. The hollow inner tubular layer may comprise PTFE or Polyimide. The hollow inner tubular layer may have a thickness of 0.1 mm.

The inner conductive layer may protrude beyond an edge of the tubular dielectric material, so that the inner conductive layer is exposed at the first end of the cable. This may facilitate connection of the electrosurgical instrument at the first end of the cable.

In an alternative configuration the cable may comprise a hollow tube of the inner conductive layer; a tube of the dielectric material on an outer surface of the hollow tube of the inner conductive layer; and a tube of the outer conductive layer on an outer surface of the tube of the dielectric material. Again, air gaps may, or may not, be present between one or more of the layers. In one example, such a configuration may be manufactured by coating the inner and outer conductive layers on the inner and outer surfaces of the dielectric material, respectively.

This cable may further comprise a protective outer tubular layer on an outer surface of the tube of the outer conductive layer. The outer tubular layer may comprise PTFE or Polyimide. The protective outer tubular layer may be an insulating layer.

The outer conductive layer may protrude beyond an edge of the tube of dielectric material, so that the outer conductive layer is exposed at the first end of the cable. This may facilitate connection of the electrosurgical instrument.

An outer diameter of the cable may be smaller over a portion (section or part) of its length adjacent to the first end of the cable. In other words, the cable may be narrower at the first end. This may facilitate connection of the cable to the electrosurgical instrument.

The outer diameter of the cable may be made smaller over the portion by reducing an internal diameter of cable. In other words, the walls of the cable may be jogged or moved inwards so that they are closer to the central axis of the cable for a section of the cable at the first end.

Alternatively, or in addition, the outer diameter of the cable may be made smaller over the portion by reducing a thickness of the dielectric material, or another component of the cable. In this case, the internal diameter of the cable may be unchanged, but the external diameter is reduced. The thickness of the dielectric material, or the other component, may be reduced by machining the region down to a smaller thickness, or by using a heat-shrink material, for example.

Radiofrequency energy and/or microwave frequency energy may be input to the cable using a side feed positioned at, or adjacent to, the second (proximal) end of the cable. This may allow a clear channel through the cable for various other components and instrument controls. In order that RF energy is not short circuited, the inner and outer conductive layers may not be connected across the dielectric material where the hollow channel exits the cable. Microwave energy may be prevented from leaking from the open end of the cable by a coaxial filter or choke. The distance of the choke or filter from the side feed may be chosen in order to match the impedance of the generator equipment to the impedance of the hollow cable and side feed.

There may be provided an electrosurgical apparatus comprising the cable according to any one of the previous claims and an electrosurgical instrument, wherein:

a first cooperating terminal of the electrosurgical instrument is electrically connected to the first terminal, so that an electrical connection is formed between the inner conductive layer and the first cooperating terminal; and a second cooperating terminal of the electrosurgical instrument is electrically connected to the second terminal, so that an electrical connection is formed between the outer conductive layer and the second cooperating terminal.

BRIEF DESCRIPTION OF THE DRAWINGS

Embodiments of the present invention will now be discussed, by way of example only, with reference to the accompanying Figures, in which.

DETAILED DESCRIPTION; FURTHER OPTIONS AND PREFERENCES

Figure 1:
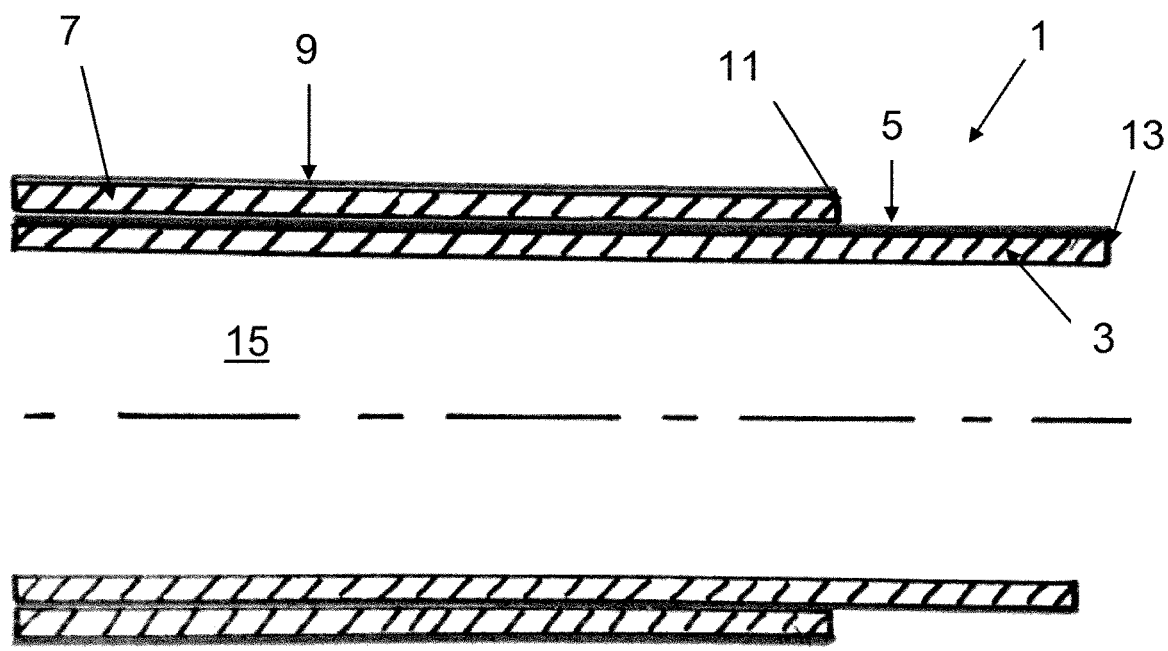
FIG. 1 is a schematic illustration of a part of a cable according to an embodiment of the present invention.

Where features of the embodiments described below are equivalent, the same reference numerals are used and detailed description thereof is not repeated.

A schematic illustration of a part of a cable according to an embodiment of the present invention is illustrated in FIG. 1. FIG. 1 only shows selected details of the cable relating to its general construction, and does not show the connection terminals of the cable. The dashed line in FIG. 1 is intended to illustrate a central axis of the cable.

The cable 1 illustrated in FIG. 1 comprises an inner tubular layer 3, which may comprise PTFE or Polyimide or another material that provides sufficient mechanical strength (the electrical properties of this layer are of less significance). In this embodiment, the inner tubular layer has a thickness of 0.1 mm.

An inner metal layer 5 (which corresponds to an inner conductive layer) is provided on an outer surface of the inner tubular layer 3, to form a tube around the inner tubular layer 3. In this embodiment, the inner metal layer 5 is made of silver and has a thickness of 0.01 mm.

A dielectric layer 7 (which corresponds to dielectric material) is provided on an outer surface of the inner metal layer 5, to form a tube around the inner metal layer 5. In this embodiment, the dielectric layer 7 comprises PTFE and has a thickness of 0.4 mm.

An outer metal layer 9 (which corresponds to an outer conductive layer) is provided on an outer surface of the dielectric layer 7, to form a tube around the dielectric layer 7. In this embodiment, the outer metal layer 9 is made of silver and has a thickness of 0.01 mm.

Of course, in other embodiments the thicknesses of any of the layers may be different to the thicknesses described above, and the material of any of the layers may also be different. For example, the dielectric layer 7 may comprise a different low-loss microwave dielectric material, or a different radiofrequency dielectric material, instead of PTFE, and the inner and/or outer metal layers 5, 9 may be formed of metal(s) other than silver.

The inner metal layer 5, dielectric layer 7 and outer metal layer 9 form a coaxial transmission line for conveying radiofrequency and/or microwave frequency energy to an electrosurgical instrument connected thereto.

The inner tubular layer 3 may act to protect the inner metal layer 5 from any components inserted through the hollow inner of the cable 1 during use of the cable. In this sense, the inner tubular layer may be considered to be a liner. The inner tubular layer 3 may also provide mechanical strength to the cable.

In other embodiments, a further insulating sleeve or coating may be provided on an outer surface of the outer metal layer 9 to prevent wear of the outer metal layer 9 during use of the cable, and to electrically insulate the outer metal layer 9.

An edge 11 of the dielectric layer 7 (and the outer metal layer 9) is set back relative to an edge 13 of the inner tubular layer 3 (and the inner metal layer 5), so that a region of the inner metal layer 5 is exposed between the edges 11, 13. This may facilitate connection of an electrosurgical instrument at the end of the cable. However, this is not essential.

In some embodiments, the edge of the outer metal layer 9 may be set back relative to the edge 11 of the dielectric layer 7, in order to increase an air gap between the outer metal layer 9 and the inner metal layer 5. This may reduce the risk of electrical breakdown of the air between the outer metal layer 9 and the inner metal layer 5 occurring.

Alternatively, or in addition, in some embodiments an insulating fluid or grease or other material may be applied at or around the edge of the outer metal layer 9, and/or in other areas of the cable, to reduce the risk of electrical breakdown of air occurring in the cable.

In one embodiment, the structure shown in FIG. 1 may be constructed by sequentially forming each layer on an outer surface of the previous (inner) layer. For example, an outer surface of the inner tubular layer 3 may be coated with metal to form the inner metal layer 5. The set back position of the edge 11 may be achieved by machining this edge back, for example. Alternatively, this configuration may be manufactured by forming the inner metal layer 5 on an outer surface of the inner tubular layer 3, forming the outer metal layer 9 on an outer surface of the dielectric layer 7, and then inserting the inner tubular layer 3 inside the dielectric layer 7.

The cable shown in FIG. 1 has a central channel, bore or lumen 15 through which components, such as a liquid or gas feed, or a pull-wire or other control means, can be fed and supplied to an electrosurgical instrument connected to the cable.

Figure 2:
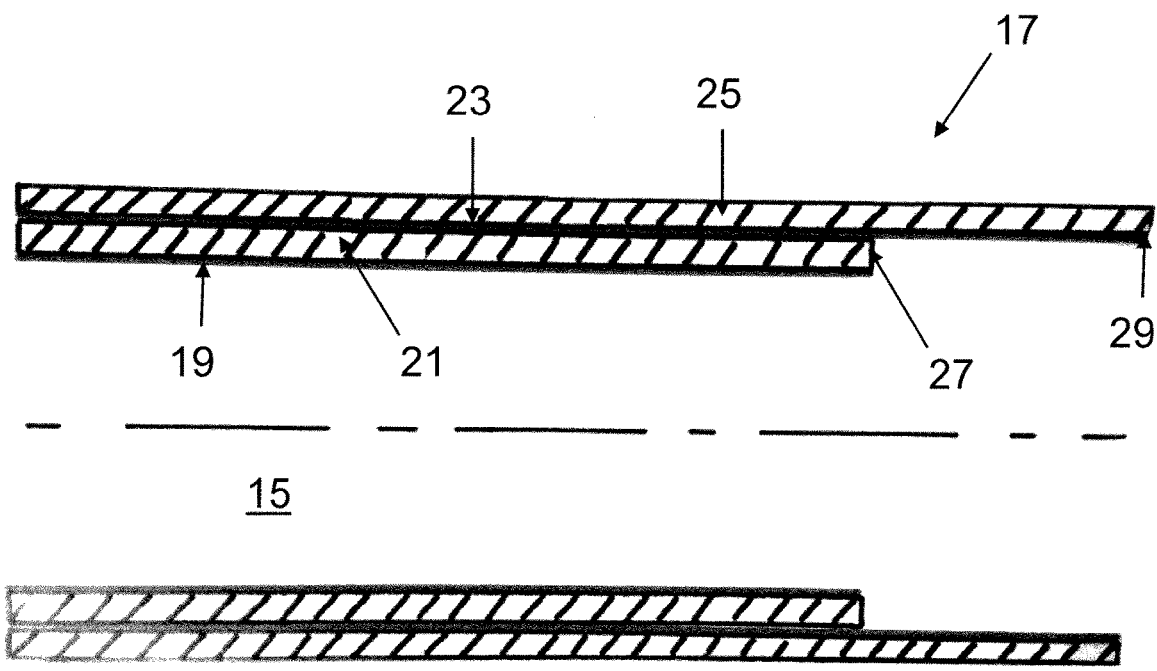
FIG. 2 is a schematic illustration of a part of a cable according to an alternative embodiment of the present invention.

A schematic illustration of a part of a cable according to an alternative embodiment of the present invention is illustrated in FIG. 2. FIG. 2 only shows selected details of the cable relating to its general construction, and does not show the connection terminals of the cable. The dashed line in FIG. 2 is intended to illustrate a central axis of the cable.

The cable 17 illustrated in FIG. 2 comprises an inner tubular metal layer 19 (which corresponds to an inner conductive layer). In this embodiment, the inner tubular metal layer 19 is made of silver and has a thickness of 0.01 mm.

A dielectric layer 21 (which corresponds to dielectric material) is provided on an outer surface of the inner tubular metal layer 19, to form a tube around the inner tubular metal layer 19. In this embodiment, the dielectric layer 21 comprises PTFE and has a thickness of 0.4 mm.

An outer metal layer 23 is provided on a surface of the dielectric layer 21. In this embodiment the outer metal layer 23 comprises silver and has a thickness of 0.01 mm.

An outer tubular layer 25 is provided on a surface of the outer metal layer 23. In this embodiment the outer tubular layer 25 comprises PTFE or Polyimide and has a thickness of 0.1 mm.

Of course, in other embodiments the thicknesses of any of the layers may be different to the thicknesses described above, and the material of any of the layers may also be different. For example, the dielectric layer 21 may comprise a different low-loss microwave dielectric material, or a different radiofrequency dielectric, instead of PTFE, and the inner and/or outer metal layers 19, 23 may be formed of metal(s) other than silver.

The inner metal layer 19, dielectric layer 21 and outer metal layer 23 form a coaxial transmission line for conveying radiofrequency and/or microwave frequency energy to an electrosurgical instrument connected thereto.

An edge 27 of the dielectric layer 21 (and the inner metal layer 19) is set back relative to an edge 29 of the outer metal layer 23 (and the outer tubular layer 25), so that a region of the outer metal layer 23 is exposed between the edges 27, 29. This may facilitate connection of an electrosurgical instrument at the end of the cable. However, this is not essential.

In one embodiment, this structure may be manufactured by sequentially coating each layer on the preceding (inner) layer. The set back position of the edge 27 may be achieved by machining this edge back, for example. Alternatively, this structure may be manufactured by forming the inner metal layer 19 on an inner surface of the dielectric layer 21, forming the outer metal layer 23 on an inner surface of the outer tubular layer 25, and then inserting the dielectric layer 21 inside the outer tubular layer 25

Figure 3:
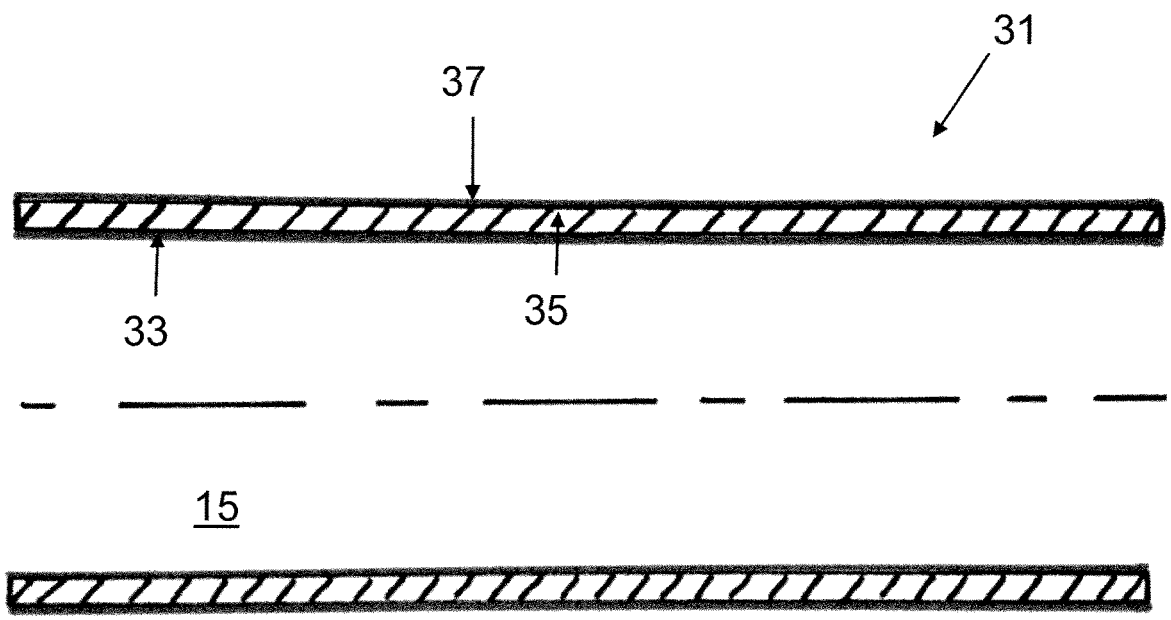
FIG. 3 is a schematic illustration of a part of a cable according to an alternative embodiment of the present invention.

A schematic illustration of a part of a cable according to an alternative embodiment of the present invention is illustrated in FIG. 3. FIG. 3 only shows selected details of the cable relating to its general construction, and does not show the connection terminals of the cable. The dashed line in FIG. 3 is intended to illustrate a central axis of the cable.

The cable 31 illustrated in FIG. 3 comprises an inner tubular metal layer 33 (which corresponds to an inner conductive layer). In this embodiment, the inner tubular metal layer 33 is made of silver and has a thickness of 0.01 mm.

A dielectric layer 35 (which corresponds to dielectric material) is provided on an outer surface of the inner tubular metal layer 33, to form a tube around the inner tubular metal layer 33. In this embodiment, the dielectric layer 35 comprises PTFE and has a thickness of 0.4 mm.

An outer metal layer 37 (which corresponds to an outer conductive layer) is provided on a surface of the dielectric layer 35. In this embodiment the outer metal layer 37 comprises silver and has a thickness of 0.01 mm.

Of course, in other embodiments the thicknesses of any of the layers may be different to the thicknesses described above, and the material of any of the layers may also be different. For example, the dielectric layer 35 may comprise a different low-loss microwave dielectric material, or a different radiofrequency dielectric material, instead of PTFE, and the inner and/or outer metal layers 33, 37 may be formed of metal(s) other than silver.

The inner metal layer 33, dielectric layer 35 and outer metal layer 37 form a coaxial transmission line for conveying radiofrequency and/or microwave frequency energy to an electrosurgical instrument connected thereto.

In one embodiment, this structure may be manufactured by coating the inner metal layer 33 and the outer metal layer 37 on the inner and outer surfaces of the dielectric layer 35, respectively. Alternatively, the inner metal layer 33 and/or the outer metal layer 37 may comprise solid metal tubes positioned on the inner or outer surface of the dielectric layer 35.

Figure 4:
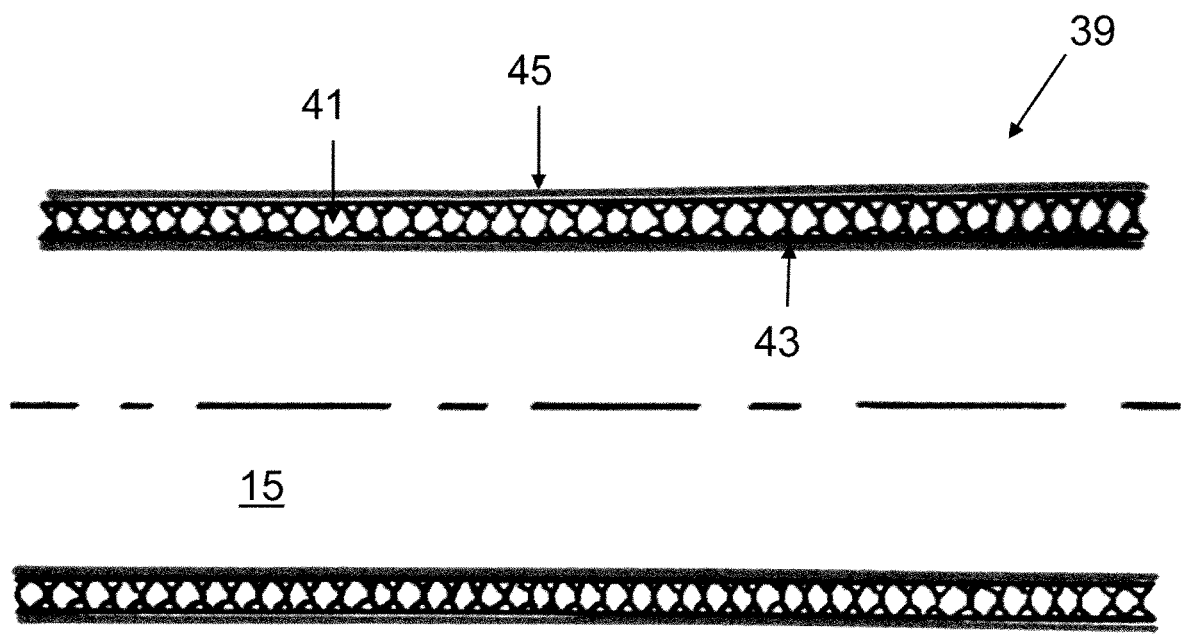
FIG. 4 is a schematic illustration of a part of a cable according to an alternative embodiment of the present invention.

A schematic illustration of a part of a cable according to an alternative embodiment of the present invention is illustrated in FIG. 4. FIG. 4 only shows selected details of the cable relating to its general construction, and does not show the connection terminals of the cable. The dashed line in FIG. 4 is intended to illustrate a central axis of the cable.

The cable 39 illustrated in FIG. 4 comprises an inhomogeneous porous structure of dielectric material 41. The inhomogeneous porous structure may be, for example, a honeycomb structure, a mesh structure, or a foam structure formed from a foam material. The dielectric material 41 may comprise PTFE.

An inner metal layer 43 is provided on an inner surface of the dielectric material 41 and an outer metal layer 45 is provided on an outer surface of the dielectric material 41.

The inner metal layer 43, dielectric layer 41 and outer metal layer 45 form a coaxial transmission line for conveying radiofrequency and/or microwave frequency energy to an electrosurgical instrument connected thereto.

The inhomogeneous porous structure of the dielectric material 41 may improve the microwave dielectric properties of the dielectric material 41. In other words, the dielectric material 41 may be a more effective low-loss microwave dielectric.

In this embodiment, one or both of the inner metal layer 43 and the outer metal layer 45 may be a solid metal tube, rather than a metal coating. This may improve the mechanical strength and structural integrity of the cable.

Alternatively, one or both of the inner metal layer 43 and the outer metal layer 45 may be a metal coating and may be formed on an additional tubular layer provided on the inner surface of the inner metal layer 43 or on the outer surface of the outer metal layer 45, to provide mechanical support for the cable. Such an additional tubular layer may be formed of PTFE or Polyimide, for example.

Figure 5:
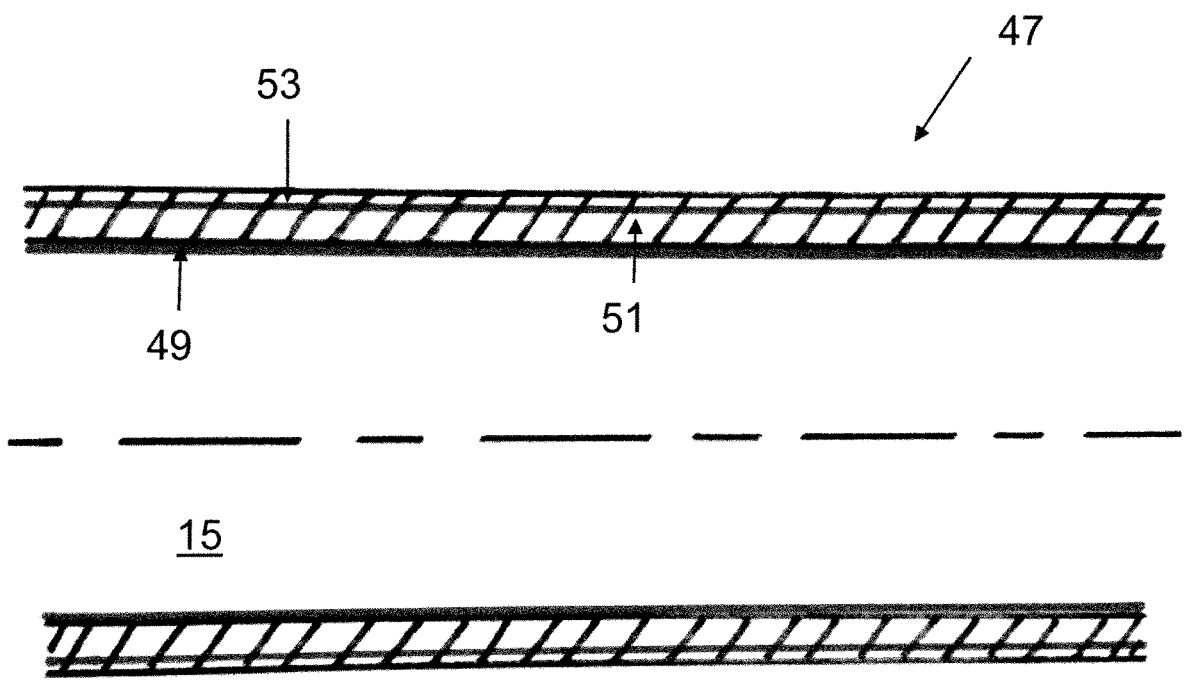
FIG. 5 is a schematic illustration of a part of a cable according to an alternative embodiment of the present invention.

A schematic illustration of a part of a cable according to an alternative embodiment of the present invention is illustrated in FIG. 5. FIG. 5 only shows selected details of the cable relating to its general construction, and does not show the connection terminals of the cable. The dashed line in FIG. 5 is intended to illustrate a central axis of the cable.

The cable 47 illustrated in FIG. 5 comprises an inner metal layer 49 and a dielectric layer 51 provided on an outer surface of the inner metal layer 49. The cable further comprises a braided metal structure 53 (which corresponds to the outer conductive layer) embedded in the dielectric layer 51.

In one embodiment, this construction may be manufactured by extruding or otherwise forming part of the dielectric layer 51 on a surface of the inner metal layer 49, braiding the braided metal structure 53 over the part of the dielectric layer 51, and then extruding or otherwise forming the remainder of the dielectric layer 51 over the braided metal structure 53.

In an alternative embodiment, the material coated on top of the braided metal structure 53 may be different from the material below (inside) the braided metal structure 53. For example, the braided metal structure 53 may be formed over a dielectric layer 51, and then a different material may be extruded or otherwise formed over the braided metal structure 53. This different material may not be a dielectric material and may instead be an insulating material such as Polyimide.

The inner metal layer 49 may comprise a solid tube of metal, or alternatively may be a metal coating, for example a silver coating, formed on an outer surface of a further tubular layer (not shown), such as a tubular layer of PTFE or Polyimide.

In this embodiment, the braided metal structure is formed by braiding copper or steel wire coated with silver. Of course, other metals may be used in other embodiments.

In this embodiment, the dielectric material comprises PTFE.

Any of the configurations disclosed above may be used in the present invention. Variations of the described embodiments may also be used. For example, in the embodiments a metal coating on the surface of a tube of material may be replaced with a solid metal tube instead, and vice versa.

In some embodiments of the present invention, the outer diameter of the cable may be reduced for part of its length near, or at, the end of the cable where the cable is attached to the electrosurgical instrument. This may facilitate connection of the cable to the electrosurgical instrument.

Figure 6:
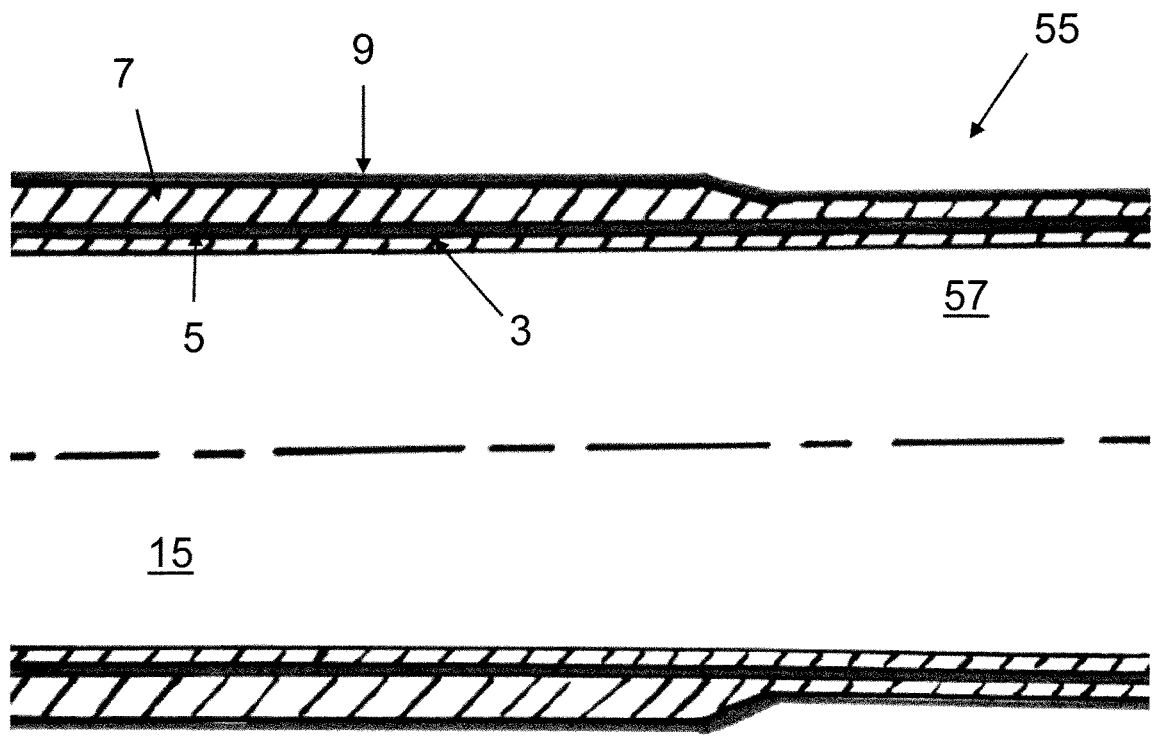
FIG. 6 is a schematic illustration of a part of a cable according to an alternative embodiment of the present invention in which an outer diameter of the cable is narrower near an end thereof.

As an example, this is illustrated in FIG. 6 for a cable with the configuration illustrated in FIG. 1. In the cable 55 illustrated in FIG. 6, the thickness of the dielectric layer 7 is reduced over a part 57 of the length of the cable 55 adjacent to the end of the cable 55. For example, the thickness of the dielectric layer 7 may be reduced from 0.4 mm to a thickness of 0.2 mm or 0.1 mm in the reduced thickness part, so that the overall diameter of the cable 55 is reduced by 0.4 mm or 0.6 mm without changing the internal diameter of the cable 55. Although not shown, the edge of the dielectric layer 7 may still be set back as illustrated in FIG. 1. In one embodiment, the thickness of the dielectric layer 7 may be reduced over a length of 20 mm adjacent to the end of the cable. The reduction in thickness may be achieved by machining down the dielectric layer 7, for example. The length of the portion of the cable having the reduced thickness may be 20 mm, for example. The maximum length of the reduced thickness portion that can be used in practice (in terms of acceptable power losses in the cable) depends on the specific thickness of the dielectric material and the electrical properties of the dielectric material. This may be determined for a particular configuration by simulation and/or measurement.

The same effect may be achieved in the other embodiments by reducing the thickness of one or more of the dielectric material and the other tubular layer if present so as to reduce the outer diameter of the cable at the end of the cable where the electrosurgical instrument is connected.

Alternatively, or in addition, the outer diameter of the cable may be reduced in the part near the end where it is connected to the electrosurgical device by reducing an internal diameter of the cable.

Figure 7:
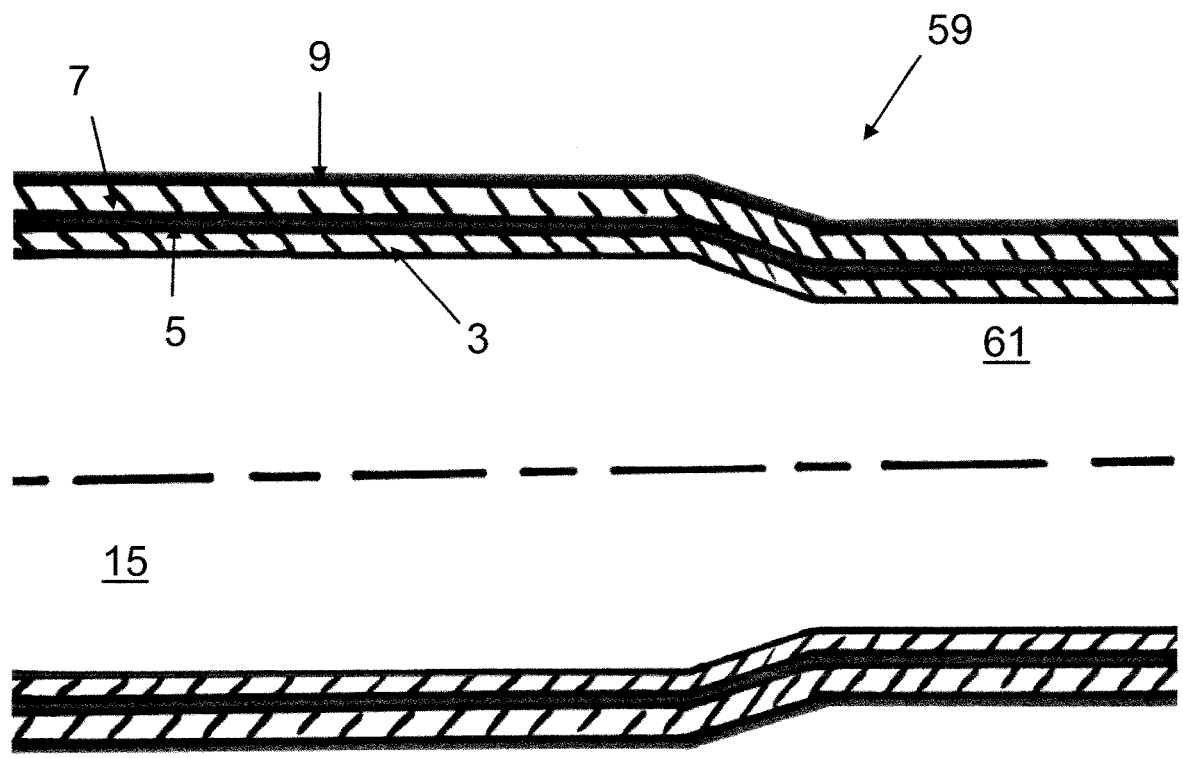
FIG. 7 is a schematic illustration of a part of a cable according to an alternative embodiment of the present invention in which in which an outer and an inner diameter of the cable are narrower near an end thereof.

As an example, this is illustrated in FIG. 7 for a cable with the configuration illustrated in FIG. 1. In the cable 59 illustrated in FIG. 7, the internal diameter of the cable is reduced over a part 61 of the length of the cable 59 by deflecting or moving the outer wall of the cable 59 inwards in the part 61 so that an inner diameter of the cable 59 is reduced. The length of the cable having the reduced thickness may be 20 mm, for example.

The same effect can be achieved with the other embodiments described above by moving the wall of the cable inwards to reduce an inner diameter of the cable.

In any of the described embodiments, if the cable is for conveying radiofrequency energy only the dielectric material may be a suitable radiofrequency dielectric material, such as Kapton, or Kapton Polyimide, i.e. a dielectric material with a breakdown strength that is sufficiently greater than the voltage of the radiofrequency energy.

In some embodiments of the present invention, both radiofrequency energy and microwave frequency energy are conveyed using the inner and outer metal layers. However, there may be a risk in some cases of the higher voltage radiofrequency signals causing electrical breakdown of the dielectric material. Thus, in some embodiments of the present invention, radiofrequency signals may be conveyed to the electrosurgical instrument separately from the microwave frequency signals. This may be achieved by conveying the radiofrequency energy using the inner metal layer and/or the outer metal conductor and a conductor positioned in, and extending along, the hollow bore in the cable.

Figure 8:
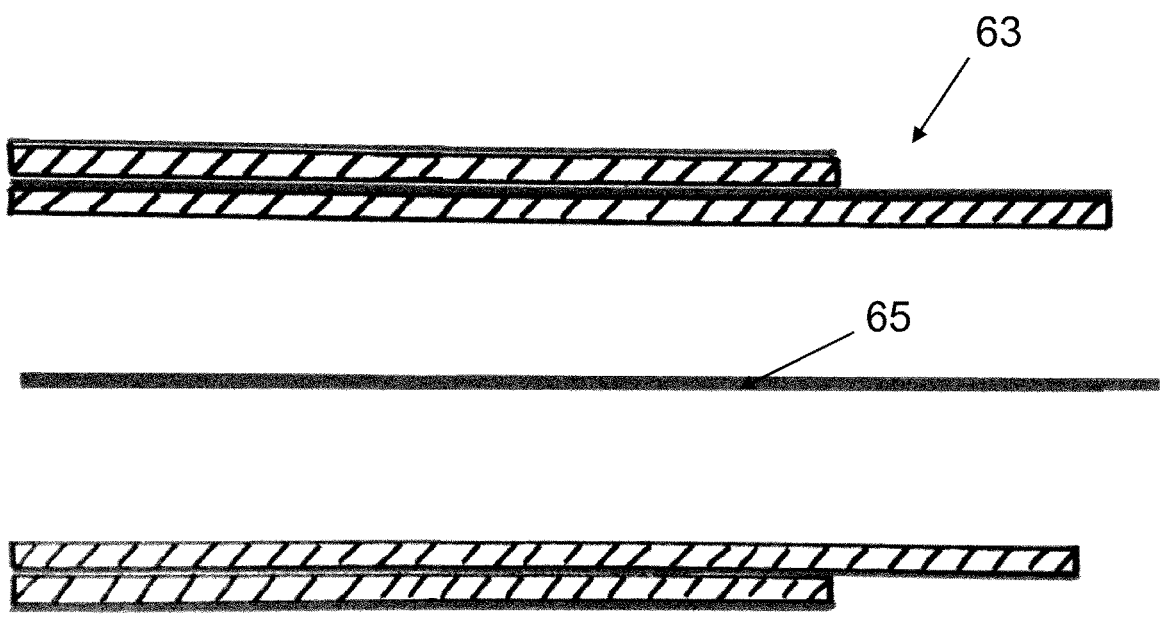
FIG. 8 is a schematic illustration of a cable according to an embodiment of the present invention in which radiofrequency energy is conveyed using a conductor inside the hollow cable.

This is illustrated in FIG. 8 for a cable with the configuration illustrated in FIG. 1. However, the same concept also applies to the other configurations described above, i.e. a conductor may be positioned in the hollow core of the other configurations and used to convey radiofrequency energy. In the cable 63 illustrated in FIG. 8, a conductor 65 is positioned in the hollow core of the cable 63 and extends along the cable 63 to the electrosurgical instrument (not shown). In some embodiments, the conductor 65 may be a metal rod or tube provided for this purpose. However, in other embodiments the conductor 65 may be a conductive outer surface of a part of the electrosurgical instrument, or of a component such as a tube for supplying liquid or gas, or a housing for a guide- or pull-wire or other control means.

The conductor 65 is insulated from the inner and outer metal layers of the cable by the inner tubular layer. For example, the inner tubular layer may comprise an insulating material.

The cable 63 can be connected to a generator configured to supply a radiofrequency signal to the cable through the conductor 65 and the inner metal layer and/or outer metal layer and a microwave frequency signal through the inner metal layer and the outer metal layer. Thus, the dielectric material may not experience sufficient voltage to cause it to electrically break down, because it may only be exposed to lower voltage microwave frequency signals.

The inner metal layer and the outer metal layer may be electrically connected together at a second (proximal) end of the cable when both the inner and outer metal layers are used to convey the radiofrequency energy together with the central conductor 65.

With this arrangement, it may be necessary to provide one or more components at the end of the cable where it connects to the electrosurgical instrument to prevent the radiofrequency signal from being able to travel back along the microwave transmission path of the inner and outer metal layers, and/or to prevent the microwave signals from travelling back along the conductor 65. Otherwise, the dielectric material may still be exposed to high voltage signals and may still be at risk of break down.

Alternatively, or additionally, in one embodiment the cable may be configured so that the conductor 65 can be pulled axially back along the cable to break the electrical connection between the conductor 65 and the electrosurgical instrument when only microwave frequency energy is being conveyed to the electrosurgical instrument, to prevent microwave frequency energy from travelling along conductor 65.

In order to reduce the risk of electrical breakdown of the dielectric or air gaps occurring in any of the above described embodiments a low-loss fluid or grease or other material may be provided around one or more parts of the cable, for example at likely breakdown areas such as at the ends of one or more of the layers, to reduce the risk of electrical breakdown occurring.

Some specific examples of how to connect the cable to an electrosurgical instrument will now be discussed. Although these specific examples each relate to one of the configurations discussed above, the same features and concepts may be applied to the other configurations discussed above.

Figure 9A:
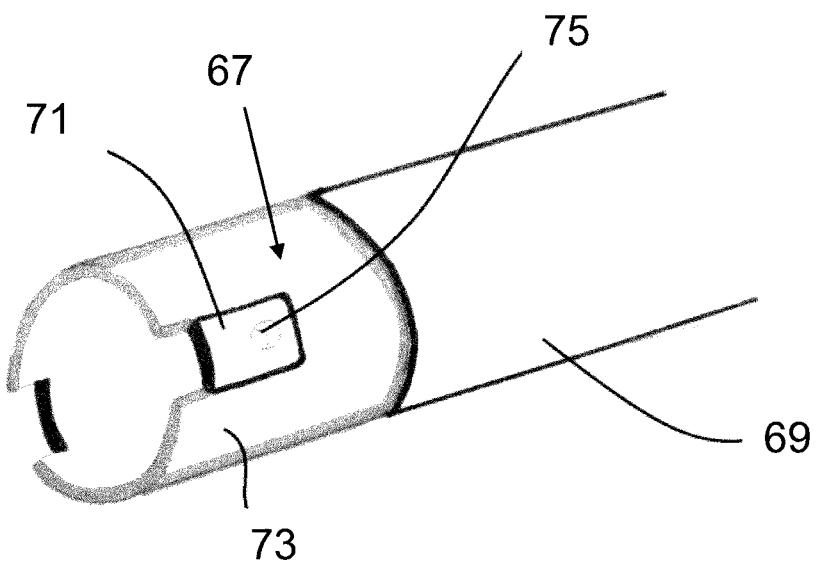
FIGS. 9A to 9D show a first configuration of the electrical connection terminals of a cable according to an embodiment of the present invention.
Figure 9B:
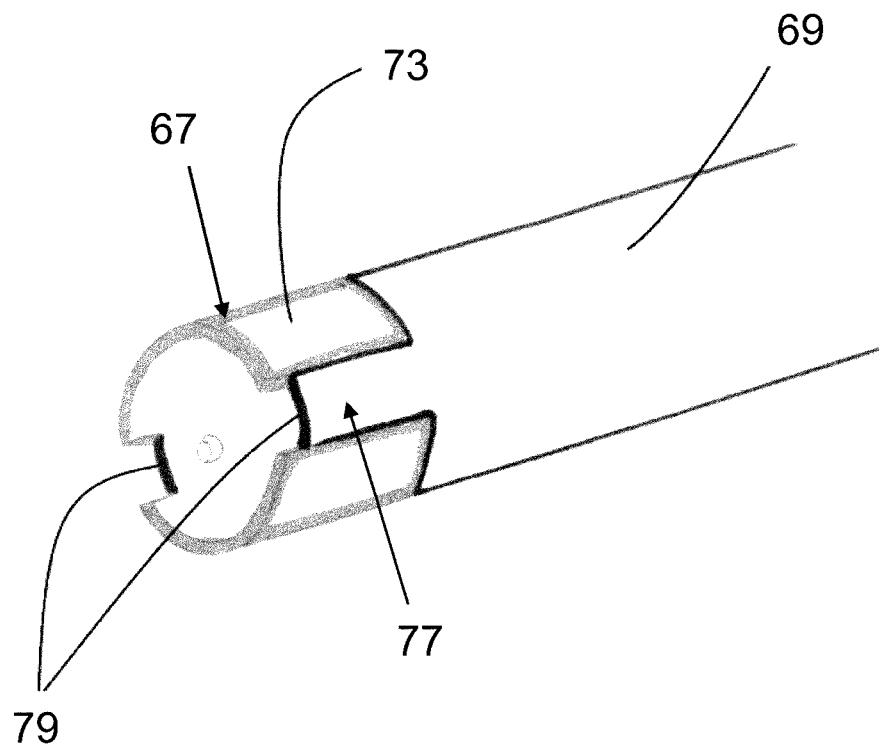
Figure 9C:
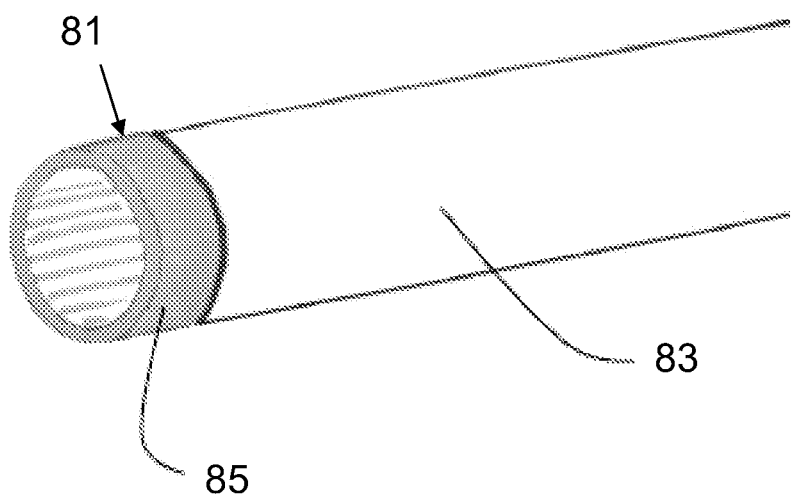
Figure 9D:
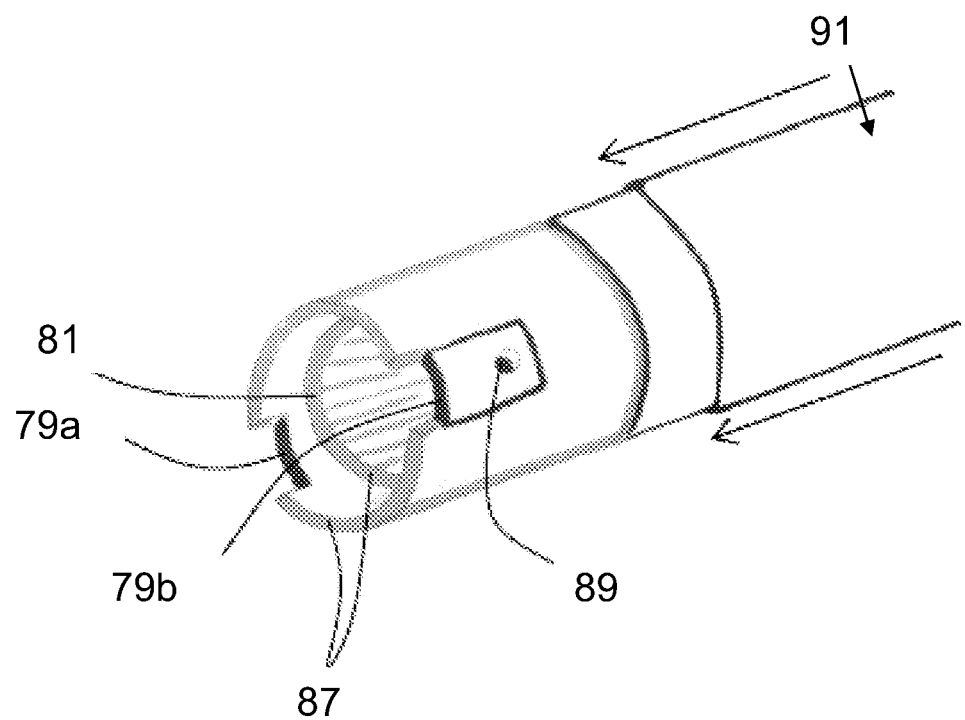

FIGS. 9A to 9D show a first configuration of the first and second connection terminals of a cable according to an embodiment of the present invention. FIGS. 9A to 9C illustrate how the cable having this configuration may be manufactured, and FIG. 9D shows the configuration of the first and second terminals in this embodiment.

FIG. 9A is a schematic illustration of a front view of a first end of a tube of dielectric material 67. The dielectric material 67 may comprise PTFE, for example. The tube of dielectric material 67 has a tubular metal coating 69 (which corresponds to an outer conductive layer) on its outer surface that extends from near the edge of the first end to a second end of the tube of dielectric material 67 (not shown). The tube of dielectric material 67 also has an electrically isolated first conductive area 71 on its outer surface, which comprises an electrically isolated metal coating.

In one embodiment, the electrically isolated first conductive area 71 may initially be formed as a part of the tubular metal coating 69 and then areas 73 of the tubular metal coating 69 may be selectively removed, for example by etching, to leave the electrically isolated first conductive area 71. For example, the area 73 in FIG. 9A may be an area where the tubular metal coating 69 has been selectively removed. Of course, in other embodiments the electrically isolated conductive area 71 may be formed by selectively coating the electrically isolated first conductive area 71 and not the surrounding area 73.

The electrically isolated first conductive area 71 may correspond to a first terminal, or a first area of electrically conductive material.

In this embodiment, the first conductive area has a rectangular shape, but this is not essential.

A hole 75 (or bore or channel) is formed in the electrically isolated first conductive area 71 and also through the tube of dielectric material 67 beneath the electrically isolated first conductive area 71.

FIG. 9B is a schematic illustration of a back view of the first end of the tube of dielectric material 67 (from the opposite side to FIG. 1). Opposite to the location of the electrically isolated first conductive area 71 on the front side is a second conductive area 77 that is electrically connected to the tubular metal coating 69.

The second conductive area 77 may correspond to a second terminal, or to a second area of electrically connected material.

The second conductive area 77 may be formed by removing, for example etching, the tubular metal coating 69 away in the surrounding region 73, or by selectively forming the metal coating in the second conductive area 77 but not in the surrounding area 73. The second conductive area 77 has a rectangular shape.

As shown in FIGS. 9A and 9B, on the end face of the cable the outward facing edge of the cable is coated with conductive material at the tabs 79, which are adjacent to and electrically connected to the first conductive area 71 and the second conductive area 77 respectively. Thus, the first conductive area 71 and the second conductive area 77 are exposed at the end face of the cable.

FIG. 9C is a schematic illustration of a further tube of material 81, which may be made of PTFE of Polyimide, for example. The further tube of material 81 may correspond to an inner tubular layer. The further tube of material 81 has a tubular metal coating 83 (which corresponds to an inner conductive layer) on its outer surface that extends from near to the edge of the first end to a second end of the further tube of material 81 (not shown). On a portion 85 of the surface of the further tube of material 81 no metallic coating is present. The portion 85 may be produced by removing, for example etching, the tubular metallic coating 83 in that area.

FIG. 9D is a schematic illustration of the resulting cable that is produced when the further tube of material 81 is inserted into the tube of dielectric material 67 and fixed so that its front edge is a few millimetres behind the front edge of the tube of dielectric material 67, in a staggered arrangement 87. Of course, in practice the cable illustrated in FIG. 9D may be made in a different way to this, for example by selectively forming each layer of the cable on a previous layer of the cable, to build up the structure of the cable. For example, each layer may be coated or extruded on a preceding layer, and selective parts of one or more layers may be removed where necessary, for example by etching.

In the configuration shown in FIG. 9D, the hole 65 in the first conductive area 71 is located directly over the tubular metal coating 83 of the further tube of material 81. The hole 65 is filled with a conductive material 89, so that an electrical connection is made between the first conductive area 71 and the tubular metal coating 83 of the further tube of material 81.

Therefore, accessible on the outer circumferential surface of the cable is a first conductive area 71 (a first terminal) that is electrically connected to the inner tubular metal layer 83 and a second conductive area 77 (a second terminal) that is electrically connected to the outer tubular metal layer 69. These conductive areas 71, 77 are positioned on opposite sides of the cable.

Furthermore, a first tab 79a (a second terminal) on the front face of the cable is electrically connected to the second conductive area 77 and a second tab 79b (a first terminal) on the front face of the cable is electrically connected to the first conductive area 71. Therefore, an electrosurgical instrument may be brought into bipolar electrical contact with the cable by bringing corresponding terminals on a front face of the electrosurgical instrument into direct contact with the tabs 79a and 79b.

Alternatively, or in addition, the electrosurgical instrument may have protruding parts that overlap and contact the first conductive area 71 and the second conductive area 77 respectively.

Furthermore, the staggered arrangement 87 of the edges of the further tube of material 81 and the tube of dielectric material 67 provides a good surface for attaching an electrosurgical instrument without having to go larger than the outer diameter of the cable or smaller than the inner diameter of the cable at the connection point.

A protective sheath 91 may be provided over the outer surface of the cable to protect the outer conductive layer 69 and/or to insulate the outer conductive layer. Alternatively, a protective coating, for example a spray coating, may be applied to the outer conductive layer 69 to protect and/or to insulate the outer conductive layer.

In the structure illustrated in FIG. 9D, the microwave frequency signal is conveyed from the inner conductive layer 83 to the first conductive area 71, which is at a greater diameter than the inner conductive layer 83. This change in diameter of the microwave frequency signal path risks causing an impedance mismatch that may lead to some of the microwave frequency power being reflected, so that the microwave frequency power received by the electrosurgical instrument is reduced.

In order to try to reduce such an impedance mismatch, for a given configuration of the electrosurgical instrument the geometry (for example length and/or width and/or position) of the first conductive area and/or the second conductive area may be selected, for example based on the results of simulations and/or tests and/or measurements, to substantially match the impedance of the cable to the impedance of the electrosurgical instrument. By substantially matching the impedance of the cable to the impedance of the electrosurgical instrument, the reflection of microwave frequency power at the connection interface may be minimised. This matching may be designed to be optimal at a specific microwave frequency of interest, i.e. the microwave frequency used by the electrosurgical instrument.

Figure 10A:
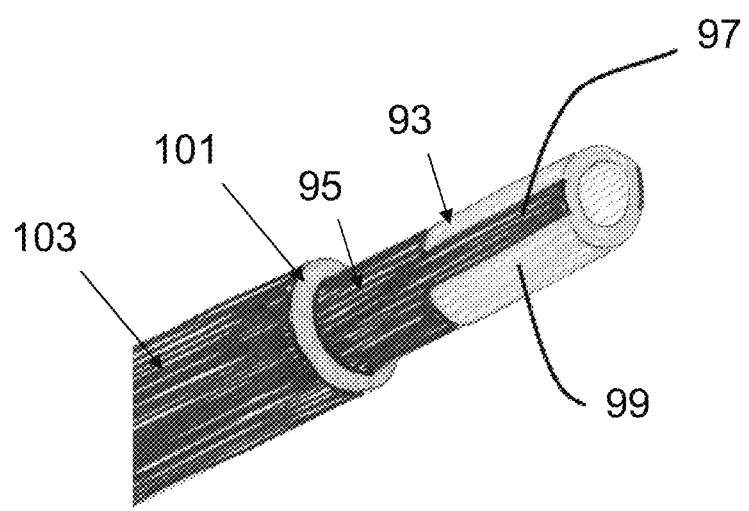
FIGS. 10A to 10C show a second configuration of the electrical connection terminals of a cable according to an embodiment of the present invention.
Figure 10B:
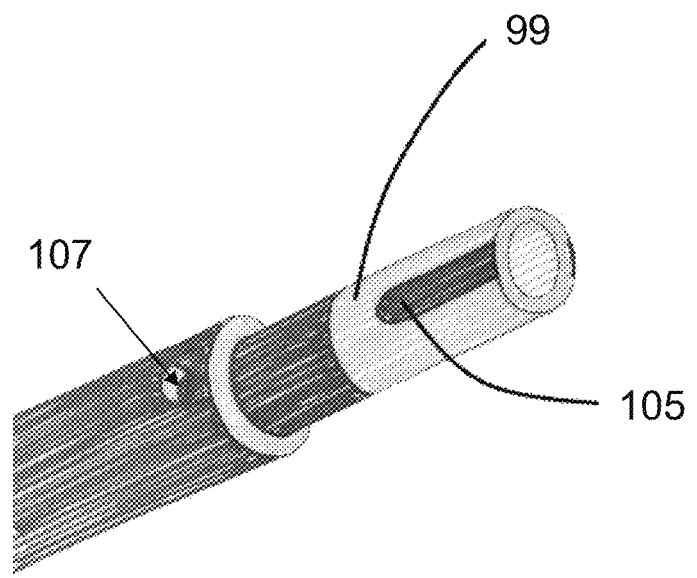
Figure 10C:
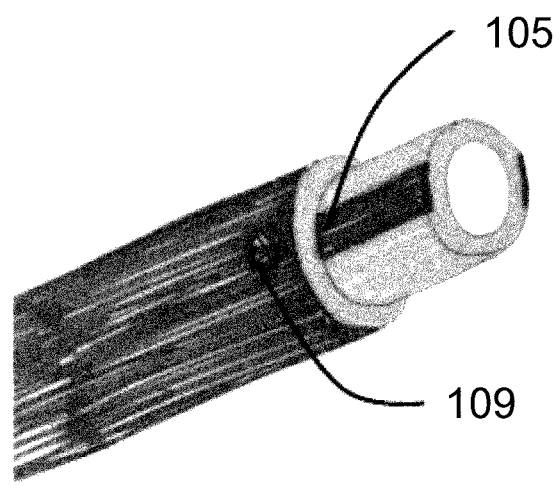

FIGS. 10A to 10C show a second configuration of the first and second connection terminals of a cable according to an embodiment of the present invention. FIGS. 10A and 10B illustrate how a cable having this construction may be manufactured, and FIG. 10C shows the configuration of the first and second terminals in this embodiment.

FIG. 10A is a schematic illustration of a front side of a first end of the cable during its manufacture. As shown in FIG. 10A, the cable comprises an inner tubular layer 93. A tubular conductive layer 95 (which corresponds to the inner conductive layer) is formed on the outer surface of the inner tubular layer 93 close to the first end and extends to a second end of the inner tubular layer 93 (not shown). A first conductive area 97 that is electrically connected to the tubular conductive layer 95 is also formed on the outer surface of the inner tubular layer 93 at the first end. The first conductive area 97 is surrounded on two sides by a region 99 in which no conductive layer is formed. In one embodiment, the first conductive area 97 may be formed by removing, for example etching, the tubular conductive layer 95 in the region 99.

As shown in FIG. 10A, the cable further comprises a tubular dielectric layer 101 which has a tubular conductive layer 103 (which corresponds to an outer conductive layer) on its outer surface. In FIG. 10A, the inner tubular layer 93 is partially inserted inside the tubular dielectric layer 101.

FIG. 10B is a schematic illustration of a back side of the first end of the cable during its manufacture (the opposite side to FIG. 10A). As shown in FIG. 10B, opposite to the first conductive area 97 on the front side is an electrically isolated second conductive area 105 that is separated from the tubular conductive layer 95 by the region 99 in which no conductive layer is formed.

The second conductive area 105 may be formed by removing, for example etching, the tubular conductive layer 95 in the surrounding area 99. Alternatively, the second conductive area 105 may be formed by selectively coating conductive material in the second conductive area 105 but not in the surrounding area 99.

As shown in FIG. 10B, the tubular dielectric layer 101 and the tubular conductive layer 103 have a through hole 107 that passes there-through close to the edge of the tubular dielectric layer 101.

FIG. 10C is a schematic illustration of the back side of the completed construction of the cable wherein the inner tubular layer 93 has been further inserted into the tubular dielectric layer 101 so that the through hole 107 is positioned over the second conductive area 105. The through hole 107 has been filled with conductive material 109 so that the outer tubular conductive layer 103 is electrically connected to the second conductive area 105 on the inner tubular layer 93.

Thus, on the inner tubular layer 93 is a first conductive area 97 (a first terminal) electrically connected to the inner conductive layer 95 and a second conductive area 105 (a second terminal) electrically connected to the outer conductive layer 103.

In an alternative embodiment, the through-hole 107 and the conductive material 109 may be omitted. Instead, conductive material may be provide on the front face of the dielectric layer 101 to electrically connect the tubular conductive layer 103 to the second conductive area 105. Thus, an electrical connection may be made between the second conductive area 105 and the tubular conductive layer 103 around the dielectric layer 101, instead of through the dielectric layer 101.

As with the previously described embodiment, the configuration (size and/or shape and/or position) of the first and/or second conductive areas 97, 105 may be selected for a given configuration of the electrosurgical instrument to try to match the impedance of the cable to the impedance of the electrosurgical instrument, to reduce reflection of microwave frequency power at the connection interface.

Figure 10D:
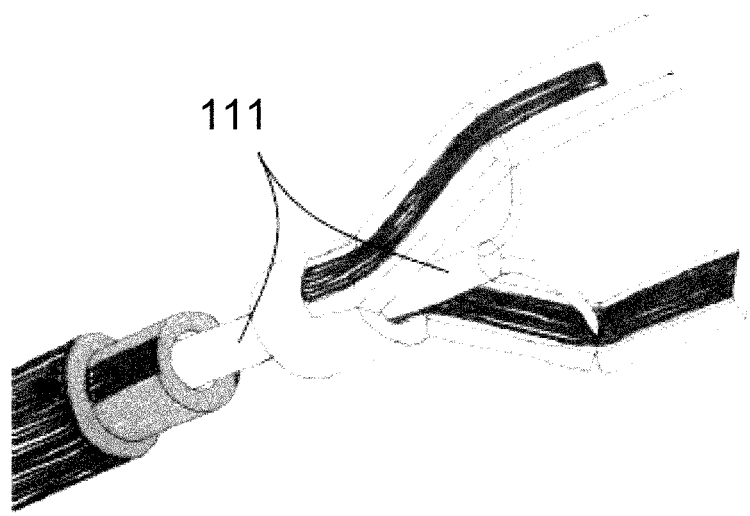
FIGS. 10D and 10E show the cable of FIG. 10C with electrosurgical instruments being connected.

FIG. 10D shows an example of a first electrosurgical tool being connected to the end of the cable. When the electrosurgical tool is fully inserted over the end of the cable, corresponding terminals inside the shaft of the electrosurgical tool (not shown) will overlap and be in direct contact with the first or second conductive areas 97, 105, thereby forming a bipolar electrical connection between the cable and the electrosurgical instrument. As further shown in FIG. 10D, in this example the electrosurgical tool comprises forceps, and a pull wire 111 and/or other controls for actuating the forceps has been passed through the centre of the hollow cable.

Figure 10E:
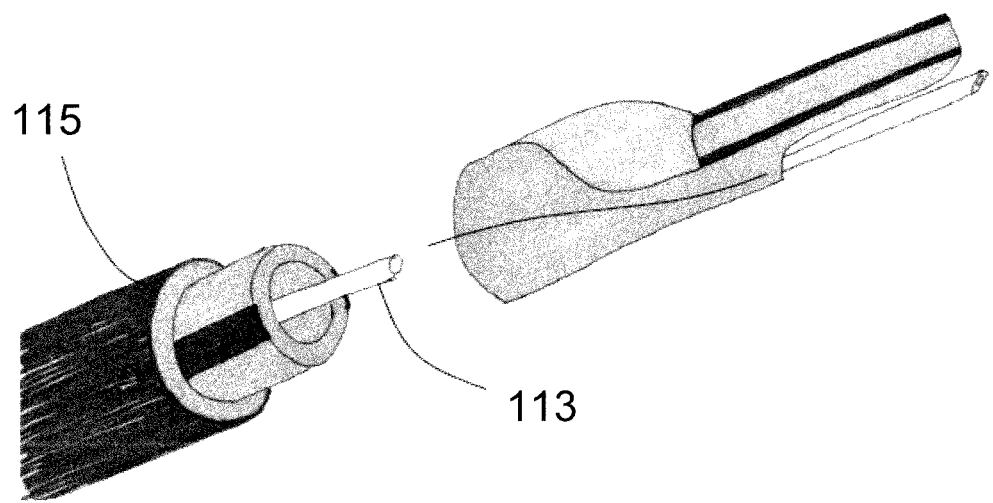

FIG. 10E shows an example of a second electrosurgical instrument being connected to the end of the cable, the electrical connection being the same as that described above. In this case, a tube 113 for supplying saline to the electrosurgical instrument has been passed through the centre of the cable 115. The tube 113 may also be used as a push rod for actuating a needle of the electrosurgical instrument.

Figure 11A:
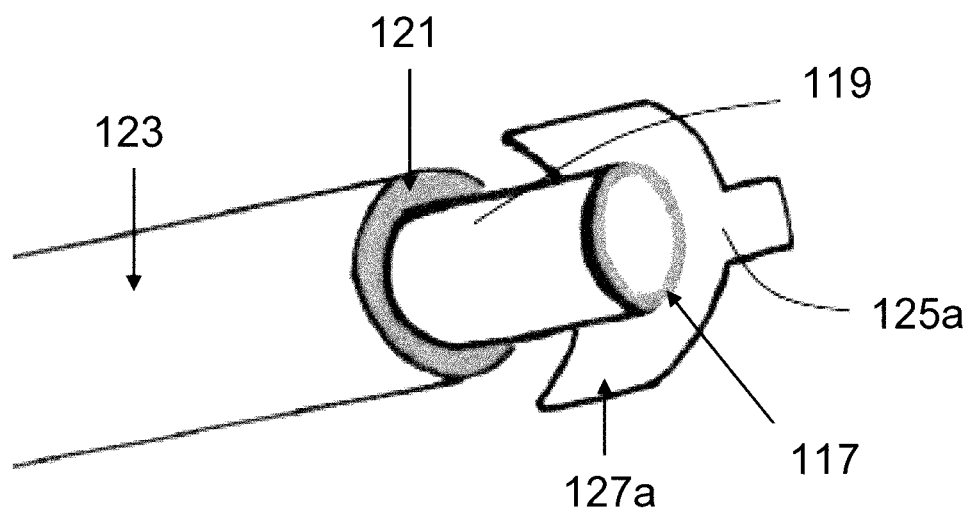
FIGS. 11A to 11E show a third configuration of the electrical connection terminals of a cable according to an embodiment of the present invention.
Figure 11B:
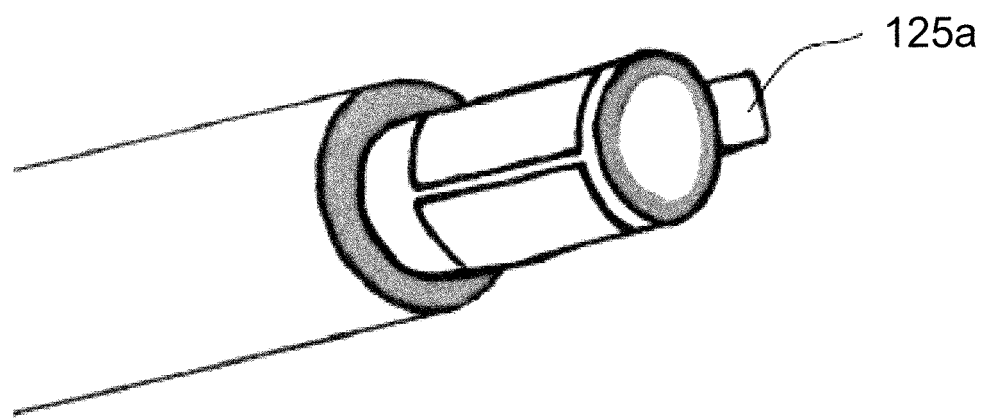
Figure 11C:
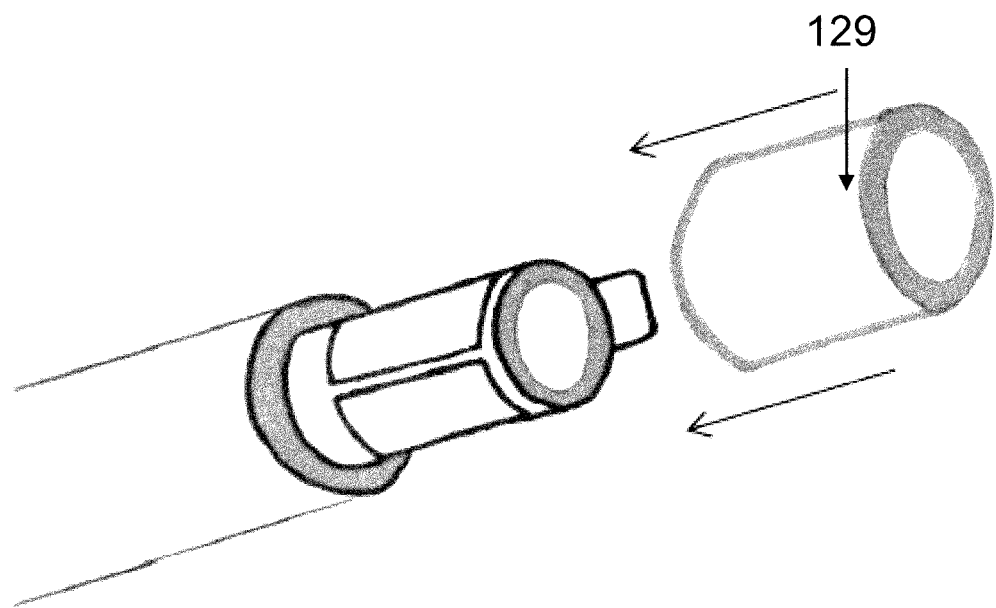
Figure 11D:
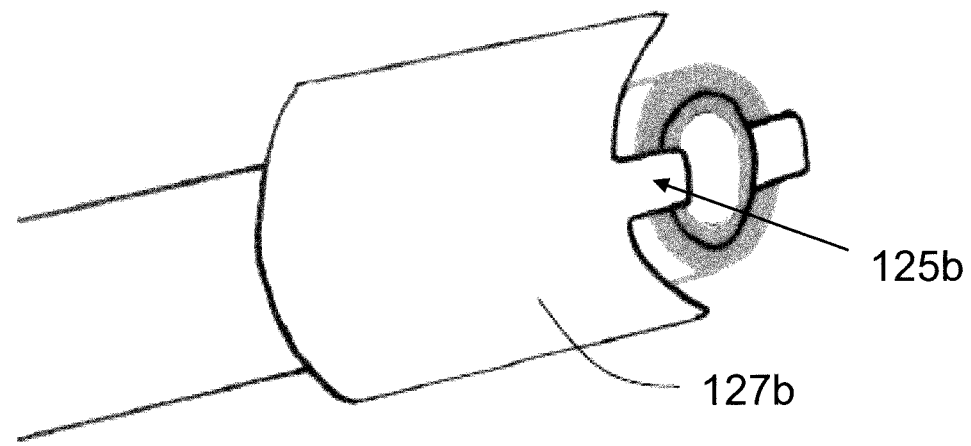
Figure 11E:
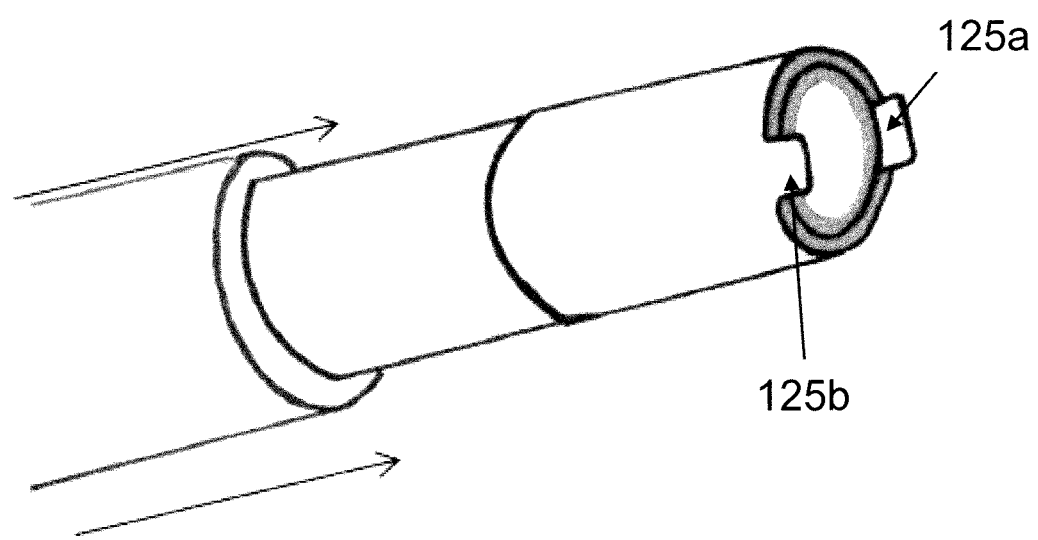

FIGS. 11A to 11E show a third configuration of the first and second connection terminals of a cable according to an embodiment of the present invention. FIGS. 11A to 11D illustrate how a cable having this construction may be manufactured. FIG. 11E shows the configuration of the first and second terminals in this embodiment.

FIG. 11A is a schematic illustration of an end of the cable. The cable illustrated in FIG. 11A comprises an inner tubular layer 117, which for example may comprise PTFE, Polyimide or another suitable material. A first tubular conductive layer 119 (which corresponds to an inner conductive layer) is coated on an outer surface of the inner tubular layer 117. The inner tubular layer 117 in FIG. 11A is partially inserted into a tube of dielectric material 121 that has a second tubular conductive layer 123 (which corresponds to an outer conductive layer) coated on its outer surface. As shown in FIG. 11A, in this arrangement a length of the inner tubular layer 117 and first tubular conductive layer 119 protrude from the tube of dielectric material 121. This configuration may be manufactured, for example, by forming a uniform cable and then cutting back the tube of dielectric material 121 and the second tubular conductive layer 123 to expose the first tubular conductive layer 119.

FIG. 11A shows a metal foil comprising a tab 125a (which corresponds to a first conductive protrusion) and an integral strip 127a being brought into contact with the first tubular conductive layer 119 by the strip 127a being wrapped around the first tubular conductive layer 119 with the tab 125a protruding in the axial direction from the end of the cable. The metal foil may be bonded to the first tubular conductive layer 119.

FIG. 11B shows the same configuration illustrated in FIG. 11A but with the strip 127a in position wrapped around the first tubular conductive layer 119.

FIG. 11C shows the configuration illustrated in FIG. 11B with a short section of a tube of dielectric material 129 being slid over the end of the cable so that it covers the metal foil and so that it is flush with an edge of the inner tubular layer 117.

FIG. 11D shows a second metal foil also comprising a tab 125b (which corresponds to a second conductive protrusion) and an integral strip 127b being brought into contact with the second tubular conductive layer 123 by the strip 127b being wrapped around the second tubular conductive layer 123, and around the short section of tube of dielectric material 129, with the tab 125b protruding in the axial direction from the end of the cable. The metal foil may be bonded to the second tubular conductive layer 123 and/or to the short section of tube of dielectric material 129.

As shown in FIG. 11E, the resulting cable has a first tab 125a protruding in an axial direction from an end face of the cable that is electrically connected to the first tubular conductive layer 119, and a second tab 125b protruding in an axial direction from an end face of the cable that is electrically connected to the second tubular conductive layer 123. In this embodiment, the tabs protrude parallel to the axial direction of the cable. However, in other embodiments the tabs may protrude at an angle to the axial direction, so that they protrude in both the axial direction and an outward direction.

An electrical connection between the cable shown in FIG. 11E and an electrosurgical instrument may be made by bringing a face of the electrosurgical instrument into contact with the face of the cable so that the first tab 125a and the second tab 125b are received in corresponding recesses formed in the face of the electrosurgical instrument, the corresponding recesses being connection terminals of the electrosurgical instrument. In this way, a bipolar electrical connection may easily be made between the cable and the electrosurgical instrument.

As shown in FIG. 11E, a protective sheath may also be provided over the cable, to protect the second tubular conductive layer 123 and the outer metal tab, and/or to insulate these parts. Alternatively, another type of protective layer may be used, for example a protective coating, such as a spray on protective coating.

Of course, the configuration of the connection terminals shown in FIG. 11E may be achieved by manufacturing the cable in a different manner to that illustrated in FIGS. 11A to 11D, for example by selectively building up the structure of the cable on the inner tubular layer 117.

Figure 12A:
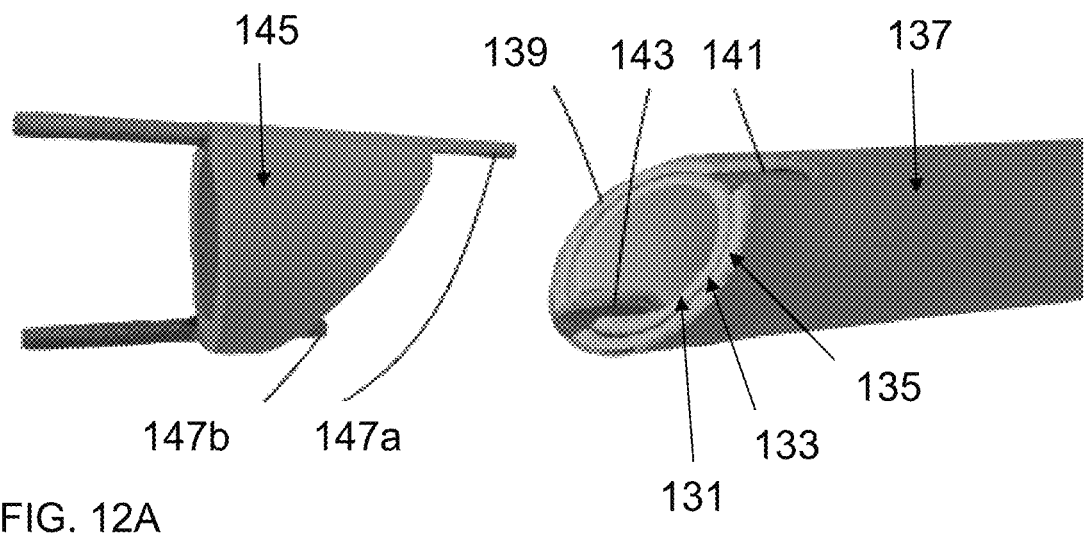
FIGS. 12A to 12C show a fourth configuration of the electrical connection terminals of a cable according to an embodiment of the present invention.
Figure 12B:
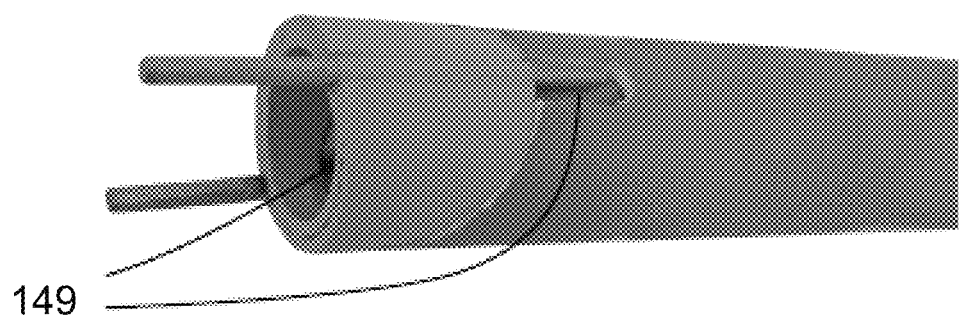
Figure 12C:
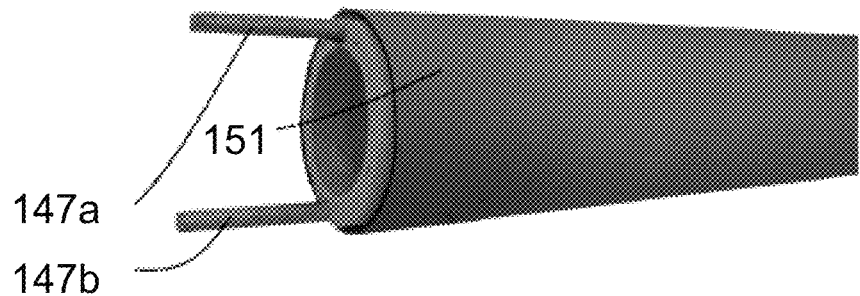

FIGS. 12A to 12C show a fourth configuration of the first and second connection terminals of a cable according to an embodiment of the present invention. FIG. 12A illustrates how a cable having this configuration may be manufactured. FIGS. 12B and 12C show the configuration of the first and second terminals in this embodiment.

FIG. 12A is a schematic illustration of an end of a cable that comprises an inner tubular layer 131, which for example may comprise PTFE, Polyimide or another suitable material. An inner conductive layer 133 is present on an outer surface of the inner tubular layer 131. A dielectric material 135 is present on an outer surface of the inner conductive layer 133. An outer conductive layer 137 is present on an outer surface of the dielectric material 135.

An end face 139 of the cable is cut at an angle, primarily so that it can be easily machined but also to give more surface area for connection to another part, as described below.

In a first region 141 of the cable, the outer conductive layer 137 and the dielectric material 135 are cut away, or otherwise removed, to expose a portion of the inner conductive layer 133. Thus, a portion of the inner conductive layer can be accessed from an external circumferential surface of the cable.

Furthermore, in a second region 143 of the cable, the inner tubular layer 131 and the inner conductive layer 133 are cut away, or otherwise removed, to expose a portion of the outer conductive layer 137. Thus, a portion of the outer conductive layer 137 can be accessed from an internal circumferential surface of the cable.

FIG. 12A also shows a short section of tube 145 that has an angled end face corresponding to, or matching, the angled end face 139 of the cable. The cable comprises attached conductive pins 147a and 147b which are positioned on the short section of tube 145 so that when the short section of tube 145 is connected to the end face 139 of the cable the first pin 147a contacts the first region 141 so that an electrical connection is formed between the first pin 147a and the inner conductive layer 133, and so that the second pin 147b contacts the second region 143 so that an electrical connection is formed between the second pin 147b and the outer conductive layer 143.

FIG. 12B shows the cable with the short section of tube 145 attached. The first region 141 and the second region 143 can be covered with an insulating adhesive 149 to insulate the exposed regions of the inner and outer conductive layers 133, 137.

As shown in FIG. 12C, an insulating outer covering 151 can also be provided around an outer surface of the cable, to protect the outer conductive layer 137 and to insulate the outer conductive layer 137. The insulating outer covering may be a sheath that is pulled over the cable, or alternatively may be a protective coating, for example a spray on coating, which is applied to the outer surface of the cable.

The resulting cable has a first conductive pin 147a protruding axially from its end face that is electrically connected to the inner conductive layer 133 and a second conductive pin 147b protruding axially from its end face that is electrically connected to the outer conductive layer 137. These pins are provided on opposite sides of the cable.

The cable may be connected to an electrosurgical instrument by bringing a face of the electrosurgical instrument into contact with the face of the cable so that the first conductive pin 147a and the second conductive pin 147b are received in corresponding recesses on the face of the electrosurgical instrument, thereby forming a bipolar electrical connection between the cable and the electrosurgical instrument.

The conductive pins 147a, 147b may provide a good electrical connection to the electrosurgical instrument and also a good mechanical connection to the electrosurgical instrument, because they are rigid and positioned on opposite sides of the cable.

In any of the configurations described above, the electrosurgical instrument may be fixed to the cable by the corresponding terminals of the electrosurgical instrument being welded (for example ultrasonically welded, spot welded, or laser welded), adhered (for example using solder or conductive epoxy such as silver epoxy) or mechanically fixed (for example by clamping or crimping, or by heat shrinking one or more components) to the terminals of the cable.

Alternatively, it may be desirable to use the same cable with more than one type of electrosurgical instrument. Therefore, the electrosurgical instrument may not be permanently attached to the cable. Instead, the corresponding terminals of the electrosurgical instrument may be brought into contact with the terminals of the cable without being fixed to them, for example by a conductive protrusion of the cable being received in a recess of the electrosurgical instrument, or vice versa. Thus, it may be possible to interchange the electrosurgical instrument attached to the cable with other electrosurgical instruments easily and quickly.

Figure 13:
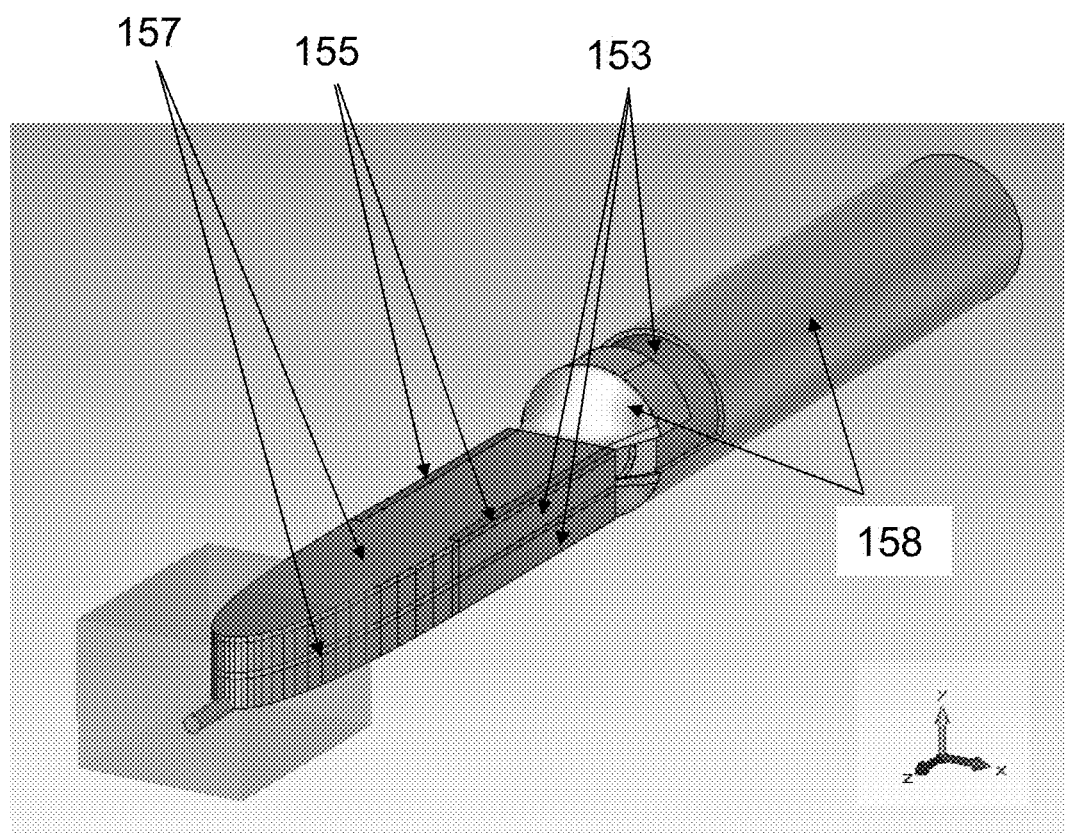
FIG. 13 shows a computer simulation of the conveyance of microwave frequency energy to an electrosurgical instrument using a cable according to an embodiment of the present invention.

FIG. 13 shows a computer simulation of the conveyance of microwave frequency energy to an electrosurgical instrument using a cable according to an embodiment of the present invention. In the computer simulation of FIG. 13, the regions 153 correspond to dielectric material. In the coaxial cable, the dielectric material is PTFE, whereas in the electrosurgical instrument, which is a blade, the dielectric material is Alumina. The strips 155 are thin strips of air, which in practice may be filled with a surface coating, e.g. Parylene. The parts 157 are electrical conductors, for example gold plated copper. The parts 158 are also electrical conductors, for example silver plated copper.

The transparent cube represents blood rich tissue into which the microwave power is to be dumped to coagulate the blood.

The cable has a configuration similar to that illustrated in FIG. 1, with the outer part 158 corresponding to the outer metal layer and the inner metal layer being almost entirely obscured. In the simulation, the inner metal layer has a diameter of 1.6 mm and the outer metal layer has a diameter of 2.4 mm. The blade of the electrosurgical tool is 2 mm wide with 0.5 mm between the conductors 157. The dielectric material under the lower conductor 157 of the blade (the "hull") is 0.5 mm thick.

In the simulation the electrical connection between the cable and the electrosurgical instrument is similar to that illustrated in FIG. 9D, in which first and second conductive areas are provided on the outside circumferential surface of the cable, the first conductive area being electrically connected to the inner metal layer and electrically isolated from the outer metal layer, and the second conductive area being electrically connected to the outer metal layer and electrically isolated from the inner metal layer. These conductive areas are electrically connected to respective terminals of the electrosurgical instrument via a tapered region.

The tapered region between the cable and the blade of the electrosurgical instrument is 1 mm long. The exact shape of the top and bottom parts of the tapered region is not considered to be critical to the design, within limits.

There is a 1 mm square connecting block between the top of the outer metal layer of the cable and the upper taper of the tapered region (corresponding to the first area of conductive material). There is also a 1 mm gap before this, in which conductive material is omitted or has been removed, and a 30 degree wide slot of removed or omitted conductive material either side of the connecting block, separating the connecting block from the rest of the outer conductor. Thus, the connecting block is electrically isolated from the rest of the outer conductor.

The remaining conductors at the top and bottom of the cable before the beginning of each taper are 150 degrees wide.

Figure 14:
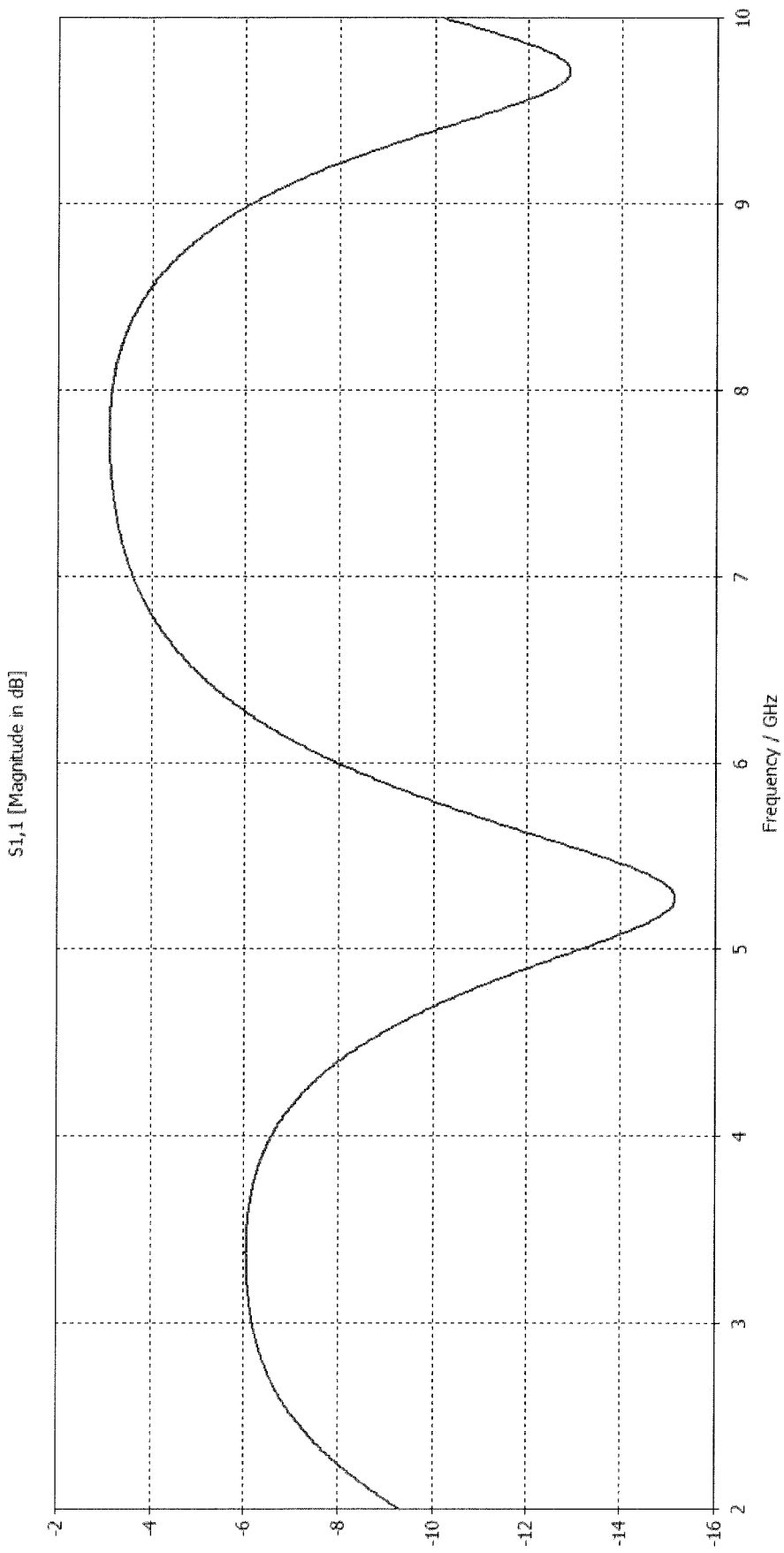
FIG. 14 shows the associated return loss as a function of frequency for the computer simulation illustrated in FIG. 13.

FIG. 14 shows the associated return loss as a function of frequency for the computer simulation illustrated in FIG. 13. The associated return loss is indicative of power loss in the cable due to reflection of power at the interface with the electrosurgical instrument, which is caused by the impedance mismatch at the interface. As shown in FIG. 14, the associated return loss is minimised with a value of roughly −10 dB at a frequency of 5.8 GHz, which in some embodiments of the present invention is the specific frequency of microwave energy conveyed by the cable.

This computer simulation demonstrates that by appropriate configuration of the first and second terminals in the present invention, for example their size and shape, the impedance of the cable can be substantially matched to the impedance of the electrosurgical instrument, thereby minimising reflection of microwave power at the connection interface.

Figure 15:
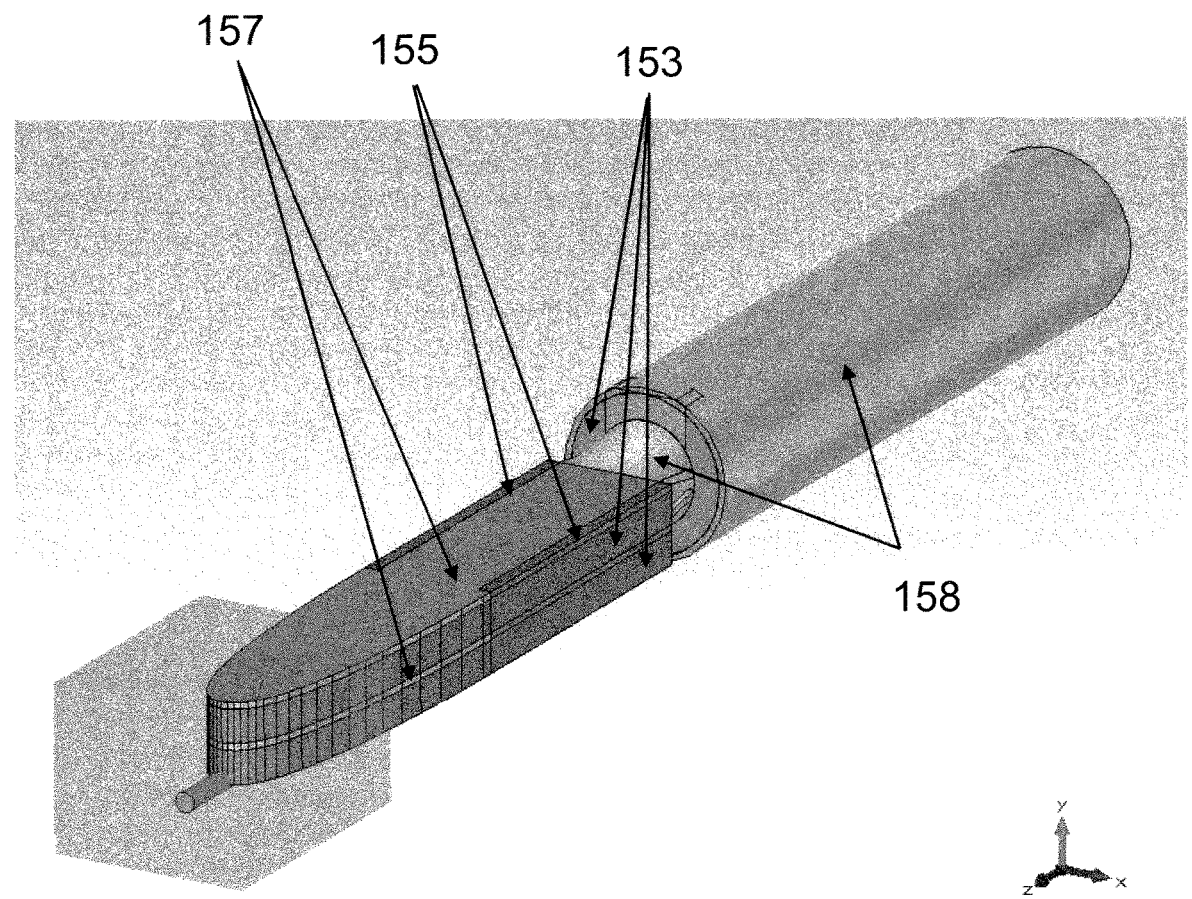
FIG. 15 shows a computer simulation of the conveyance of microwave frequency energy to an electrosurgical instrument using a cable according to an embodiment of the present invention.

FIG. 15 shows a computer simulation of the conveyance of microwave frequency energy to an electrosurgical instrument using a cable according to an embodiment of the present invention. In the computer simulation of FIG. 15, the regions 153 correspond to dielectric material. In the coaxial cable, the dielectric material is PTFE, whereas in the electrosurgical instrument, which is a blade, the dielectric material is Alumina. The strips 155 are thin strips of air, which in practice may be filled with a surface coating, e.g. Parylene. The parts 157 are electrical conductors, for example gold plated copper. The parts 158 are also electrical conductors, for example silver plated copper.

The transparent cube represents blood rich tissue into which the microwave power is to be dumped to coagulate the blood.

The configuration of the cable in this simulation corresponds to the configuration of the cable in the previous simulation, with the exception of the configuration of the electrical connection to the electrosurgical instrument.

This simulation differs from the previous simulation in that in this simulation the outer conductor has been taken down to the inner diameter (the diameter of the inner conductor) by a conductive path extending past the edge of the dielectric material separating the inner conductor from the outer conductor. The conductive path from the outer conductor to the inner diameter is 0.5 mm long and 1.3 mm wide.

The two conductors at the end of the cable are 170 degrees wide and the gaps are 10 degrees wide. The taper is 1 mm long.

In practice, the inside conductor of the cable would need a dielectric insulating coating to prevent arcing, as the edges are quite close together. This insulator would make a small difference to the associated return loss in the cable (probably an improvement).

Figure 16:
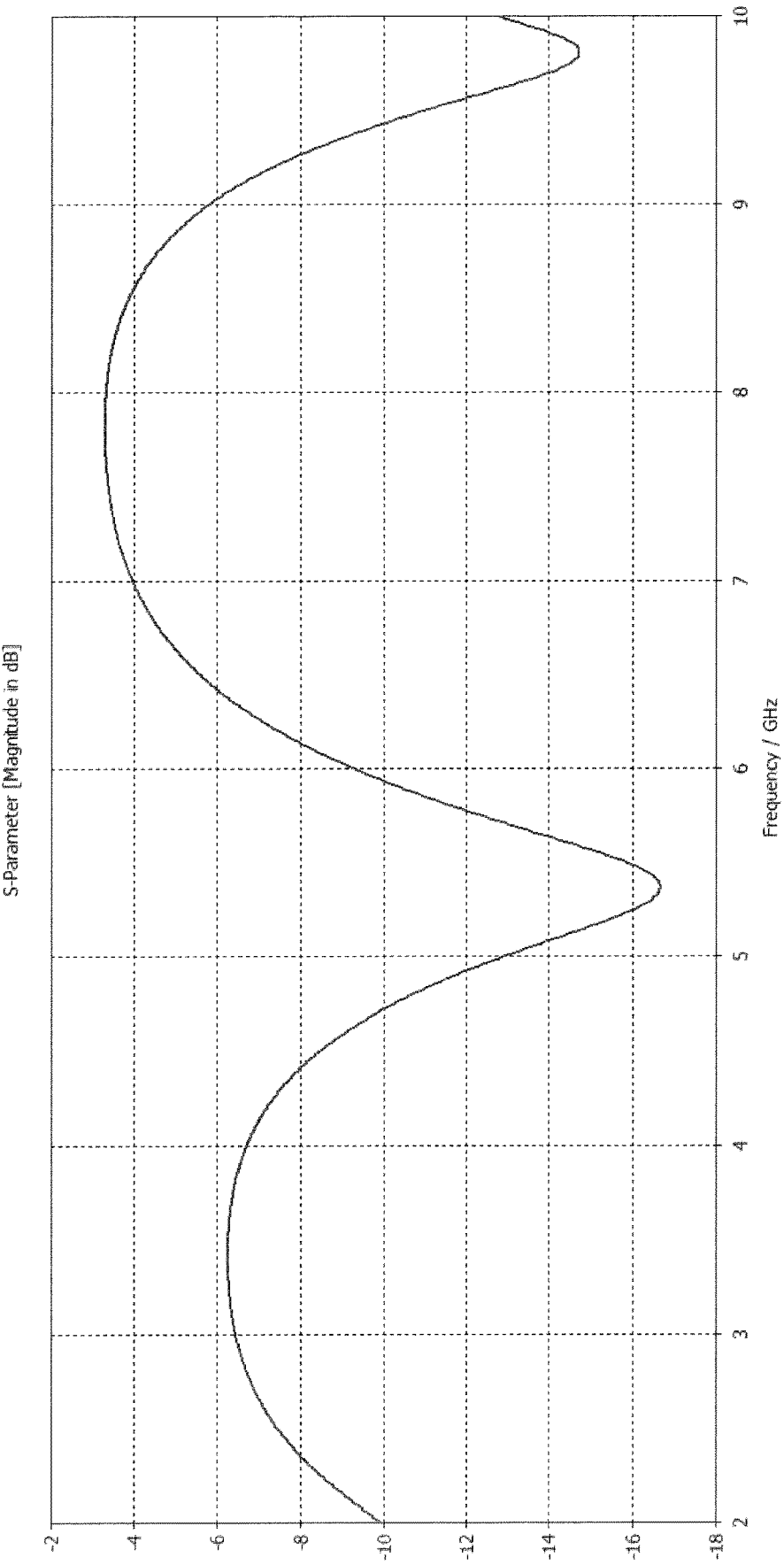
FIG. 16 shows the associated return loss as a function of frequency for the computer simulation illustrated in FIG. 15.

FIG. 16 shows the associated return loss as a function of frequency for the computer simulation illustrated in FIG. 15. The associated return loss is indicative of power loss in the cable due to reflection of power at the interface with the electrosurgical instrument, which is caused by the impedance mismatch at the interface. The associated return loss is similar to that illustrated in FIG. 14, but not identical, with the associated return loss minimised with a value of roughly −11 dB at a frequency of 5.8 GHz.

Figure 17:
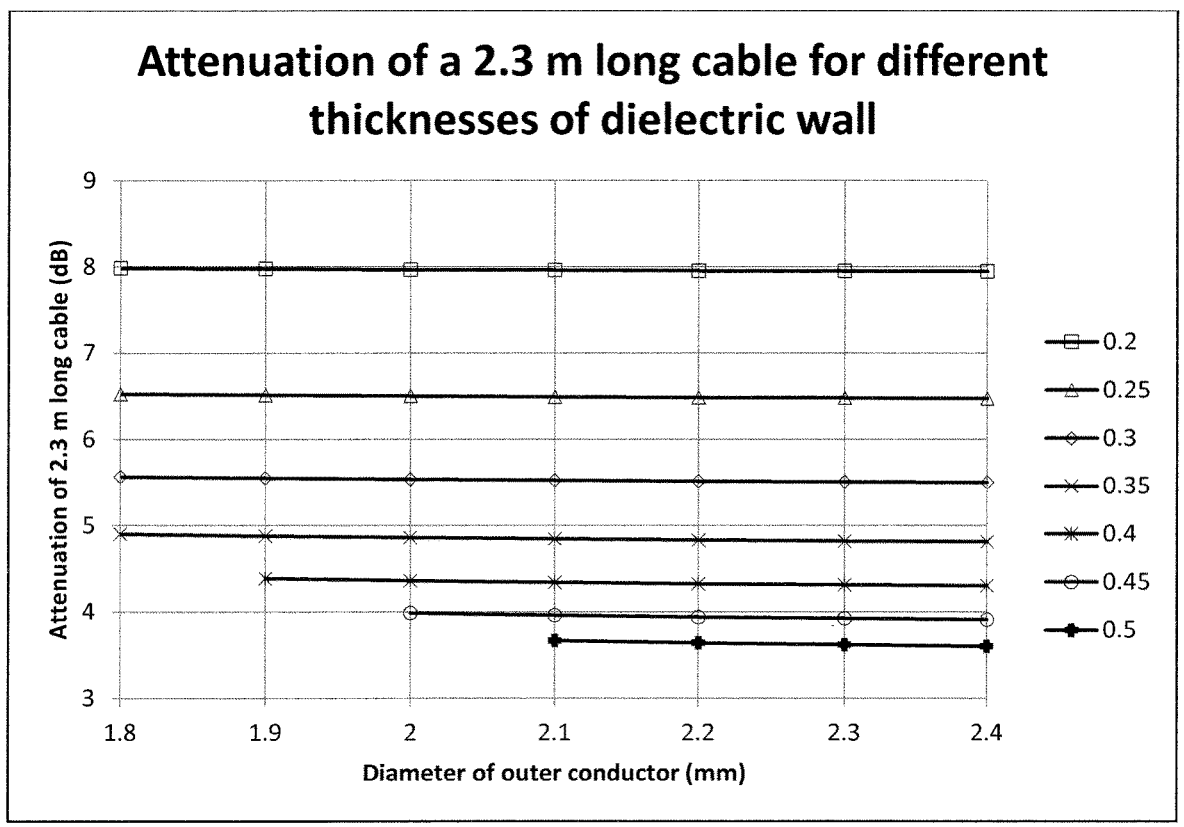
FIG. 17 is a graph showing the effect of the thickness of the dielectric layer and the diameter of the conductor on attenuation in the cable.

FIG. 17 is a graph showing the effect of the thickness of the dielectric layer and the diameter of the outer conductor on attenuation in a cable of length 2.3 m, having a configuration corresponding to that illustrated in FIG. 1. The numbers in the legend represent the thickness of the dielectric layer in mm, and these numbers are in the same order as the lines on the graph (i.e. 0.2 corresponds to the top line, 0.25 corresponds to the next line down, etc.).

FIG. 17 shows that the attenuation in the cable increases significantly with decreasing thickness of the dielectric layer, reaching a value of approximately 8 dB for a thickness of 0.2 mm and with a value of approximately 3.7 dB at 0.5 mm. It is clear from FIG. 17 that it is mainly the thickness of the dielectric layer that determines the loss, with the loss only slowly falling with increasing diameter of the outer conductor.

The invention claimed is:

1. A cable for conveying radiofrequency and/or microwave frequency energy to an electrosurgical instrument at a first end of the cable, the cable comprising:
   a hollow tube comprising inner and outer electrically conductive layers separated by dielectric material to form a transmission line, the hollow tube having a central channel extending along its length;
   a first terminal at the first end of the cable, the first terminal being arranged to form an electrical connection between the inner conductive layer and a first cooperating terminal of the electrosurgical instrument; and
   a second terminal at the first end of the cable, the second terminal being arranged to form an electrical connection between the outer conductive layer and a second cooperating terminal of the electrosurgical instrument,
   wherein the first terminal comprises a first electrically conductive protrusion extending in an axial direction from the first end of the cable and electrically connected to the inner conductive layer; and/or
   wherein the second terminal comprises a second electrically conductive protrusion extending in an axial direction from the first end of the cable and electrically connected to the outer conductive layer.

2. The cable according to claim 1, wherein the first conductive protrusion and/or the second conductive protrusion is rigid.

3. The cable according to claim 1, wherein the first conductive protrusion and/or the second conductive protrusion comprises a conductive tab, a conductive fin, a conductive rod, a conductive pin, or a conductive wire.

4. The cable according to claim 1, wherein the first terminal and the second terminal are located on opposite sides of the cable relative to a central axis of the cable.

5. The cable according to claim 1, in which the first terminal comprises the first electrically conductive protrusion, wherein the first conductive protrusion extends in the axial direction from an electrically conductive strip positioned around the inner conductive layer and electrically connected to the inner conductive layer, and wherein the first conductive protrusion is integral with the electrically conductive strip.

6. The cable according to claim 5, wherein the first conductive protrusion, and/or the second conductive protrusion, and the integral conductive strip comprise conductive foil.

7. The cable according to claim 1, in which the second terminal comprises the second electrically conductive protrusion, wherein the second conductive protrusion extends in the axial direction from an electrically conductive strip positioned around the outer conductive layer and electrically connected to the outer conductive layer, and wherein the second conductive protrusion is integral with the electrically conductive strip.

8. The cable according to claim 1, in which the cable comprises the first conductive protrusion and the second conductive protrusion, wherein the first conductive protrusion and the second conductive protrusion are supported by a tube segment connected to the first end of the cable.

9. The cable according to claim 1, in which the first terminal comprises the first electrically conductive protrusion, wherein the first conductive protrusion is electrically connected to the inner conductive layer in a region where the dielectric material and outer conductive layer are omitted.

10. The cable according to claim 1, in which the second terminal comprises the second electrically conductive protrusion, wherein the second conductive protrusion is electrically connected to the outer conductive layer in a region where the dielectric material and inner conductive layer are omitted.

11. The cable according to claim 1, wherein the geometries of the first terminal and the second terminal are configured to match the impedance of the cable to a predetermined impedance at one or more microwave frequencies.

12. The cable according to claim 1, wherein the cable comprises a conductor positioned in the hollow tube and extending along the hollow tube for conveying radiofrequency energy to the electrosurgical instrument with the transmission line.

13. The cable according to claim 1, wherein the dielectric material comprises:
a solid tube of dielectric material; or
a tube of dielectric material having a porous structure.

14. The cable according to claim 1, wherein the inner conductive layer and/or the outer conductive layer comprises:
a conductive coating on the inside or outside of a tube of material;
a solid tube of conductive material positioned against the inside or outside of a tube of material; or
a layer of braided conductive material formed on, or embedded in, a tube of material.

15. The cable according to claim 1, wherein the cable comprises:
a hollow tube of the inner conductive layer;
a tube of the dielectric material on an outer surface of the hollow tube of the inner conductive layer; and
a tube of the outer conductive layer on an outer surface of the tube of the dielectric material.

16. An electrosurgical apparatus comprising the cable according to claim 1 and an electrosurgical instrument, wherein:
a first cooperating terminal of the electrosurgical instrument is electrically connected to the first terminal, so that an electrical connection is formed between the inner conductive layer and the first cooperating terminal; and
a second cooperating terminal of the electrosurgical instrument is electrically connected to the second terminal, so that an electrical connection is formed between the outer conductive layer and the second cooperating terminal.

17. A cable for conveying radiofrequency and/or microwave frequency energy to an electrosurgical instrument at a first end of the cable, the cable comprising:
a hollow tube comprising inner and outer electrically conductive layers separated by dielectric material to form a transmission line, the hollow tube having a central channel extending along its length;
a first terminal at the first end of the cable, the first terminal being arranged to form an electrical connection between the inner conductive layer and a first cooperating terminal of the electrosurgical instrument; and
a second terminal at the first end of the cable, the second terminal being arranged to form an electrical connection between the outer conductive layer and a second cooperating terminal of the electrosurgical instrument;
wherein the first terminal comprises a first area of electrically conductive material located on a circumferential surface of the cable; and
wherein the first area of electrically conductive material is located on an outer side of the dielectric material and is electrically connected to the inner conductive layer by an electrical connection that passes through, or around, the dielectric material.

18. The cable according to claim 17, wherein the first area of electrically conductive material is exposed at an end face of the cable.

19. The cable according to claim 17, wherein the first area of electrically conductive material comprises a portion of the outer electrically conductive layer that is electrically isolated from the remainder of the outer electrically conductive layer.

20. The cable according to claim 17, wherein the electrical connection comprises a conductive material positioned in a hole through the dielectric material, or a conductive material positioned around an edge of the dielectric material.

21. The cable according to claim 17, wherein the second terminal comprises a second area of electrically conductive material located on an outer side of the dielectric material that is part of, or electrically connected to, the outer conductive layer.

22. The cable according to claim 21, wherein the first area of electrically conductive material and the second area of electrically conductive material are at different locations on a circumferential surface of the cable and are electrically isolated from each other.

23. The cable according to claim 17, wherein the cable comprises one or more protrusions or recesses for cooperating with corresponding protrusions or recesses on an end of the electrosurgical instrument for aligning the electrosurgical instrument with respect to the cable.

24. The cable according to claim 17, wherein the inner conductive layer is provided on an outer surface of a tube of material, and wherein an edge of the tube of material is set back with respect to an edge of the dielectric material.

25. A cable for conveying radiofrequency and/or microwave frequency energy to an electrosurgical instrument at a first end of the cable, the cable comprising:
a hollow tube comprising inner and outer electrically conductive layers separated by dielectric material to form a transmission line, the hollow tube having a central channel extending along its length;
a first terminal at the first end of the cable, the first terminal being arranged to form an electrical connection between the inner conductive layer and a first cooperating terminal of the electrosurgical instrument; and
a second terminal at the first end of the cable, the second terminal being arranged to form an electrical connection between the outer conductive layer and a second cooperating terminal of the electrosurgical instrument;
wherein the second terminal comprises a second area of electrically conductive material located on a circumferential surface of the cable; and
wherein the second area of electrically conductive material is located on an inner side of the dielectric material and is electrically connected to the outer conductive layer by an electrical connection that passes through, or around, the dielectric material.

26. The cable according to claim 25, wherein the second area of electrically conductive material is exposed at an end face of the cable.

27. The cable according to claim 25, wherein the second area of electrically conductive material comprises a portion of the inner electrically conductive layer that is electrically isolated from the remainder of the inner electrically conductive layer.

28. The cable according to claim 25, wherein the electrical connection comprises a conductive material positioned in a hole through the dielectric layer, or a conductive material positioned around an edge of the dielectric material.

29. The cable according to claim 25, wherein the first terminal comprises a first area of electrically conductive material located on an inner side of the dielectric material that is part of, or electrically connected to, the inner conductive layer.

30. The cable according to claim 29, wherein the first area of electrically conductive material and the second area of electrically conductive material are at different locations on a circumferential surface of the cable and are electrically isolated from each other.

* * * * *